(12) United States Patent
Schmidt et al.

(10) Patent No.: US 6,287,780 B1
(45) Date of Patent: Sep. 11, 2001

(54) COMPOUNDS FOR MASS SPECTROMETRY COMPRISING NUCLEIC ACID BASES AND ARYL ETHER MASS MARKERS

(75) Inventors: Günter Schmidt, Houghton; Andrew Hugin Thompson, Alloway; Robert Alexander Walker Johnstone, Bebington, all of (GB)

(73) Assignee: BRAX Group Limited, Cambridge (GB)

( * ) Notice: Subject to any disclaimer, the term of this patent is extended or adjusted under 35 U.S.C. 154(b) by 0 days.

(21) Appl. No.: 09/581,792
(22) PCT Filed: Dec. 18, 1998
(86) PCT No.: PCT/GB98/03842
§ 371 Date: Aug. 11, 2000
§ 102(e) Date: Aug. 11, 2000
(87) PCT Pub. No.: WO99/32501
PCT Pub. Date: Jul. 1, 1999

(30) Foreign Application Priority Data

Dec. 19, 1997 (GB) .................................................. 9726953
Jul. 13, 1998 (GB) .................................................. 9815163
Jul. 13, 1998 (GB) .................................................. 9815164
Jul. 13, 1998 (GB) .................................................. 9815166
Oct. 28, 1998 (GB) .................................................. 9823646

(51) Int. Cl.$^7$ ............................ C12Q 1/68; C07H 19/00; C07H 21/00; C07H 21/02; C07H 21/04
(52) U.S. Cl. .......................... 435/6; 536/22.1; 536/23.1; 536/24.3; 536/24.33; 536/25.3; 536/25.32
(58) Field of Search .............................. 435/6; 536/22.1, 536/23.1, 24.3, 24.33, 25.3, 25.32

(56) References Cited

FOREIGN PATENT DOCUMENTS

| 0 611 075 A | 8/1994 | (EP) . |
| 2 041 919 A | 9/1980 | (GB) . |
| WO 97/27327 | 7/1997 | (WO) . |
| WO 98/31830 | 7/1998 | (WO) . |

OTHER PUBLICATIONS

Baker et al, "Irreversible Enzyme Inhibitors. 195: Inhibitors of Thymidine Kinase from Walker 256 Carcinoma Derived from Thymidine 5'–Acetate", *Journal of Medicinal Chemistry*, vol. 15, No. 9, 1972, pp. 940–944.

Nestler et al, "A General Method for Molecular Tagging of Encoded Combinatorial Chemistry Libraries", *Journal of Organic Chemistry*, vol. 59, No. 17, 1994, pp. 4723–4724.

Ohlmeyer et al, "Complex synthetic chemical libraries indexed with molecular tags" *Proceedings of the National Academy of Sciences, USA*, vol. 90, Dec. 1993, pp. 10922–10926.

Geysen et al, "Isotope or mass encoding of combinatorial libraries", *Chemistry and Biology*, vol. 3, No. 8, Aug. 1996, pp. 679–688.

Search Report, PCT/GB98/03842, Apr. 4, 1999.

*Primary Examiner*—Jezia Riley
(74) *Attorney, Agent, or Firm*—Burns, Doane, Swecker & Mathis, L.L.P.

(57) ABSTRACT

The present invention provides a compound having the following formula: N-L-M wherein N comprises one or more nucleic acid bases, L is either a direct bond between N and M or L comprises a linker moiety, and M comprises a mass marker comprising an aryl ether.

45 Claims, 14 Drawing Sheets

NEGATIVE ION MODE GROUPS

POSITIVE ION MODE GROUPS

| NEGATIVE ION MODE GROUPS | POSITIVE ION MODE GROUPS |
|---|---|
| 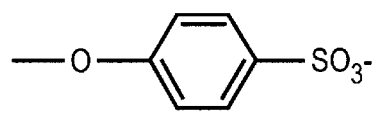 | 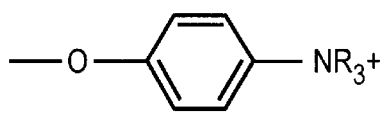 |
| 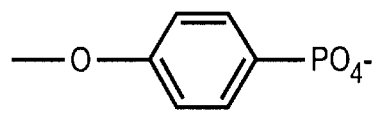 | 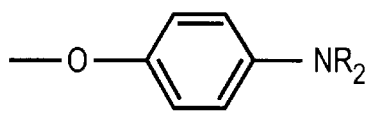 |
| 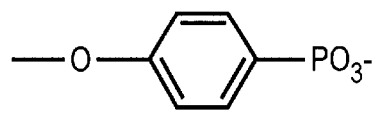 | 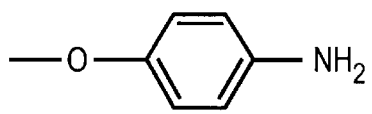 |
| 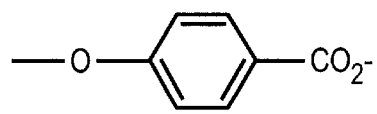 | 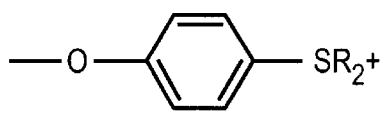 |
| | 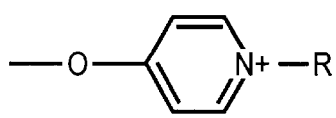 |
FIG. 1

COMPOUNDS FOR MASS SPECTROMETRY COMPRISING NUCLEIC ACID BASES AND ARYL ETHER MASS MARKERS

This invention concerns mass markers for labelling nucleic acids and other molecules. In particular the invention concerns compounds comprising specific monomeric, oligomeric and polymeric mass markers. Using this invention, mixtures of analytes can be labelled with mass markers for simultaneous detection by mass spectrometry.

At present commercially favoured detection systems for analysing nucleic acids are based on fluorescent labelling of DNA. Fluorescent labeling schemes permit the labelling of a relatively small number of molecules simultaneously, typically 4 labels can be used simultaneously and possibly up to eight. However, the costs of the detection apparatus and the difficulties of analysing the resultant signals limit the number of labels that can be used simultaneously in a fluorescence detection scheme. PCT/GB98/00127 describes arrays of nucleic acid probes covalently attached to cleavable labels that are detectable by mass spectrometry which identify the sequence of the covalently linked nucleic acid probe. The labelled probes of this application have the structure Nu-L-M where Nu is a nucleic acid covalently linked to L, a cleavable linker, covalently linked to M, a mass label. The detachable mass labels of PCT/GB98/00127, comprising the L-M components of the nucleic acid probes have a number of advantages over other methods of analysing nucleic acids. An advantage of using mass labels is the possibility of generating large numbers of labels that have discrete peaks in a mass spectrum, allowing similar numbers of distinct molecular species to be labelled simultaneously. Fluorescent dyes are expensive to synthesise whereas mass labels can comprise relatively simple polymers permitting combinatorial synthesis of large numbers of labels at low cost.

A critical feature of the mass labelled nucleic acid probes disclosed in PCT/GB98/00127 is the design of the cleavable mass labels (L-M). A number of features are required of a molecule that is to be a good mass label. A label should:

Be easily detachable from DNA.
Be fragmentation resistant in mass spectrometer.
Form a single ion peak in the mass spectrum.
Permit very sensitive detection.
Be easily distinguishable from background contamination, such as DNA. It should be clear that a mass peak is from a mass label.
Be compatible with conventional automated oligonucleotide synthesisers.
Be easy to synthesise in a combinatorial manner to minimise number of chemical steps and the number of reagents necessary to generate large number of labels.
Be compatible with existing mass spectrometry instrumentation without requiring physical modification.

Linkers to allow a mass label to be easily cleaved from its associated nucleic acid are disclosed in PCT/GB98/00127 and in GB patent application numbers 9815163.2 and 9815164.0. Compounds which improve the sensitivity of detection of a mass label by mass spectrometry are disclosed in PCT/GB98/00127 and in GB patent application number 9815166.5.

Other uses of mass modified nucleic acids are known in the art using probes with mass modifications that are not removable for direct analysis of nucleic acids by mass spectrometry. The application of mass modified peptide nucleic acids for multiplexed detection of single nucleotide polymorphisms by mass spectrometry is discussed in the following references: Ross, P. L. et al. Anal. Chem. 69:4197–4202, 1997 and Griffin, T. J. et al. Nature Biotechnology 15:1368–1372, 1997. PCT/US94/00193 discloses the use of mass modified nucleic acids in a method of DNA sequencing by mass spectrometry to permit multiplexed detection of a number of different templates.

It is thus an object of this invention to overcome problems associated with the prior art and to provide mass labelled nucleic acids that can be analysed with existing mass spectrometers. In particular, an object of this invention is to enable analysis by electrospray ionisation, thermospray ionisation, Matrix Assisted Laser Desorption Ionisation (MALDI) and tandem mass spectrometry, whether through direct analysis of mass modified nucleic acids or through analysis of labels that are cleavably detachable from their corresponding nucleic acids.

It is also an object of this invention to provide mass label entities with appropriate functionalities for attachment to nucleic acids or other analyte molecules.

It is a further object of this invention that the provided mass labels be compatible with conventional automated oligonucleotide synthesis chemistries. It is another object of this invention to provide mass labels that are compatible with the cleavable linkers disclosed in PCT/GB98/00127 and in the GB patent application numbers 9815163.2 and 9815164.0 and also mass labels that are compatible with the sensitising groups disclosed in PCT/GB98/00127 and in GB patent application number 9815166.5.

Accordingly, the present invention provides a compound having the following formula:

wherein N comprises one or more nucleic acid bases, L is either a direct bond between N and M or L comprises a linker moiety, and M comprises a mass marker comprising an aryl ether.

The invention further provides an array of mass markers, each mass marker in the array being as defined above, each set of mass markers comprising a plurality of different mass markers, each mass marker in any one set differing in mass from all other mass markers in that set by a mass of at least substantially 4 Daltons and each mass marker in any one set having the same number of aryl ether units as each of the other mass markers in that set and a different number of aryl ether units from the each of the markers in any other set.

The invention further provides a method for characterising a nucleic acid or other molecule, which method comprises identifying a mass marker by mass spectrometry, which mass marker is relatable to a specific nucleic acid base or base sequence, or a specific atom or group in a molecule, to identify the mass marker and thereby identify the base or base sequence, or the specific atom or group wherein the mass marker is as defined above.

The invention also provides use of a mass marker identifiable by mass spectrometry for the characterisation of a nucleic acid or other molecule, which mass marker is as defined above.

In certain aspects of this invention, the labels are cleavably detachable from their associated nucleic acid and are detachable by mass spectrometry. In other aspects of this invention, the labels are not cleavably detachable from their associated nucleic acid and are used to modify the mass of the analyte to which they are attached. Specifically this invention relates to compounds that can be used as mass modifying groups to generate arrays of labels or arrays of mass modified nucleic acids with distinct masses. In addition these compounds have favourable properties for use as mass labels including fragmentation resistance, thermal stability, chemical inertness and ease of ionisation.

The present invention will now be described in greater detail by way of example only, with reference to the following Figures, in which:

FIG. 1 shows a variety of solubilising and charge carrying groups that could be attached to the mass labels of this invention.

Figure 2:
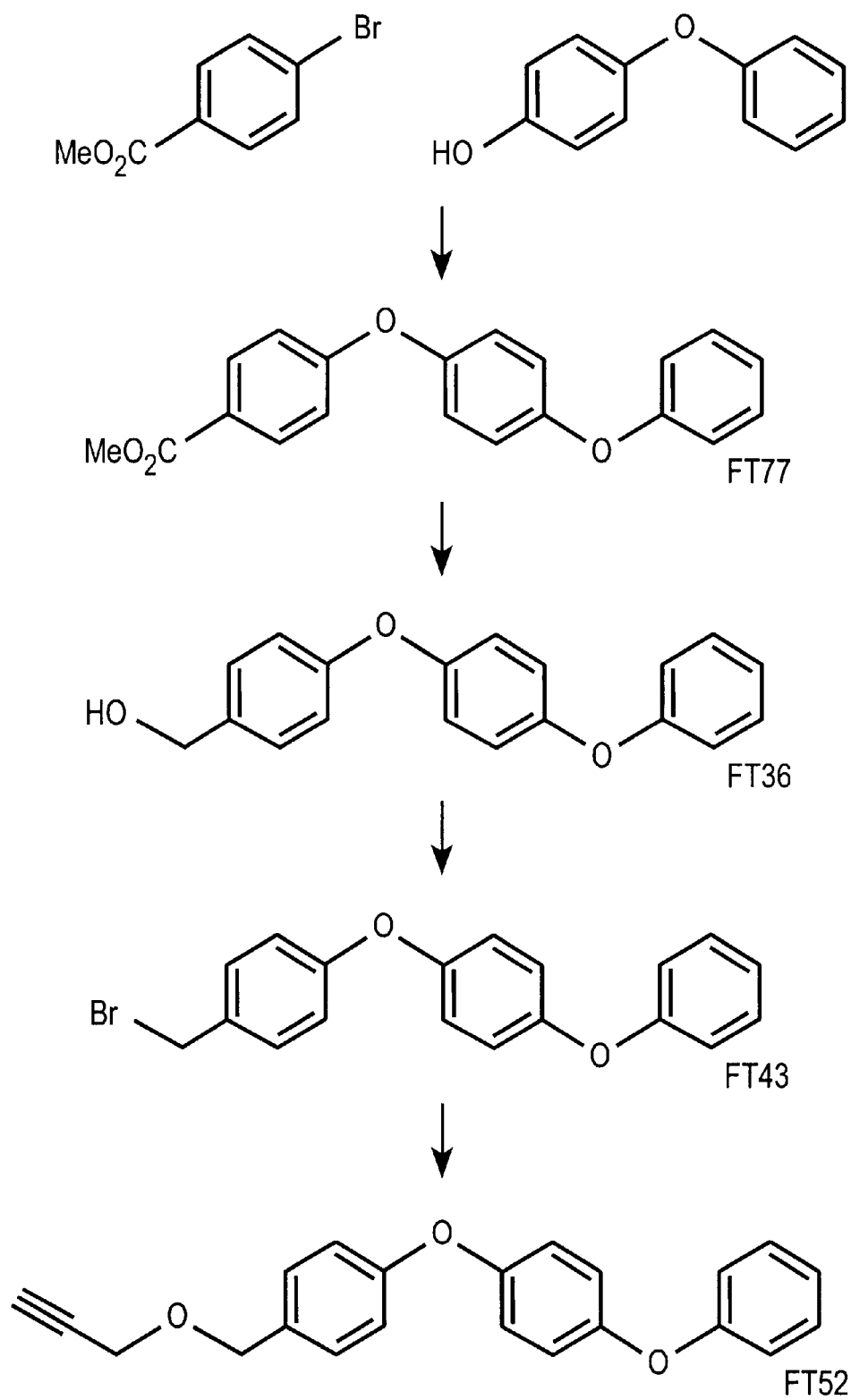
FIG. 2 shows the synthesis of trimeric poly-ethers with various reactive functionalities.

In a first aspect of this invention there is provided a mass label molecule with the following formula:

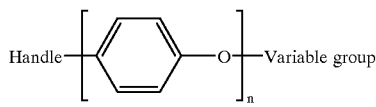

In a second aspect of this invention there is provided a mass label molecule with the following formula:

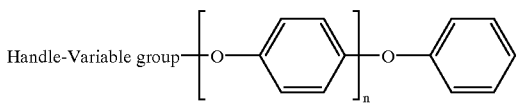

In a third aspect of this invention there is provided a mass labelled molecule with the following formula:

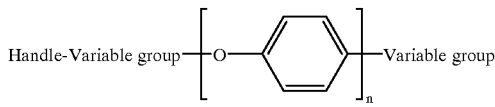

In a fourth aspect of this invention there is provided a mass labelled nucleic acid with the following formula:

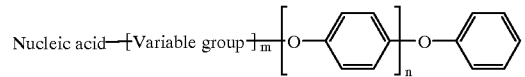

In a fifth aspect of this invention there is provided a mass label nucleic acid with the following formula:

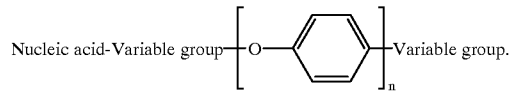

These poly-aryl-ether structures are very resistant to fragmentation and produces good negative ions since the delocalisation of electrons over the molecule can effectively stabilise a negative charge. These molecules are also thermally stable and so are particularly compatible with thermally cleaved linkers and with linkers cleaved by collision processes within the mass spectrometer. The Handle groups shown in the formulae above are reactive functionalities to allow the mass label to be reacted with a second functionality to covalently link the mass label to a molecule of interest or to variable linking groups which may give additional features to the mass label. The 'Variable Groups' shown in the formulae above may include 'mass series modifying' groups, 'mass defect' groups, linkers, which may be cleavable, solubilising groups and charge carrying groups (see FIG. 1). There may be one or more variable groups between a nucleic acid and a poly-ether polymer. There may also be one or more groups which are cleavable under predetermined conditions. Poly-ethers that comprise the polymer may be substituted with a variety of functional groups, particularly groups to change the masses of the polymers, e.g. methyl groups, fluorine or deuterium.

In the past, the general method for the synthesis of aryl ethers was based on the Ullmann-coupling of arylbromides with phenols in the presence of copper powder at about 200° C. (representative reference: H. Stetter, G. Duve, Chemische Berichte 87 (1954) 1699).

Milder methods for the synthesis of aryl ethers have been developed using a different metal catalyst but the reaction temperature is still between 100 and 120° C. (M. Iyoda, M. Sakaitani, H. Otsuka, M. Oda, Tetrahedron Letters 26 (1985) 477). This is a preferred route for the production of poly-ether mass labels. See synthesis of FT77 given in the examples below.

A very recently published method provides a most preferred route for the generation of poly-ether mass labels as it is carried out under much milder conditions than the earlier methods (D. E. Evans, J. L. Katz, T. R. West, Tetrahedron Lett. 39 (1998) 2937). FT106, FT107, and FT108 in the examples below have been prepared according to this procedure.

Mass series modifying groups introduced as variable at one end or both ends of chain of a variable number of aryl ethers are preferably substituted aryl ethers which modify the properties of the mass label. A linear polymer of aryl-ethers increases in mass by 93 mass units with each additional phenoxy residue in the molecule. To exploit the mass spectrum fully, mass labels need only be about 4 Daltons apart. To generate mass labels 4 Daltons apart each mass label preferably contains a groups that shifts the mass of each series of aryl-ethers. This Mass Series Modifying group (MSM) acts to offset each series of aryl-ether polymers from the others. With linear polymers of aryl-ethers, each monomer of which adds 93 Daltons, there will be no coincidence in mass for a maximum of 23 series if each series of mass labels is 4 mass units apart. In order to generate 256 mass labels, for example, one then needs to generate the 23 MSM groups, to link to polymers of aryl ethers with up to 12 consecutive phenoxy repeats. This will give a total of 276 mass labels.

Clearly a polymer, comprising a number of different sub-units can be generated with those sub-units appearing in different sequences. Furthermore branched structures are also possible but only linear polymers are shown for convenience of illustration. The preferred structures shown are chosen for convenience of synthesis. Different sequences of the same sub-units are not significantly more difficult to produce but it is preferable to generate as many labels as possible in as few synthetic steps as possible. A preferred synthesis strategy is to generate poly-aryl-ether polymers of up to twelve repeats and then derivitise these with a number of different MSM groups, whose masses differ ideally by about 4 Daltons to avoid overlap of isotope peaks. Variation in the MSM group can be fine-tuned by using isotopic substitutions; for example, replacement of 4 hydrogens in a molecule with 4 deuterium atoms gives a mass difference of 4 Daltons.

An advantageous embodiment of this invention where cleavable mass labels are employed is the use of fluorinated mass labels when high-resolution mass analysis of labels is employed after cleavage of mass labels from their nucleic acid. A hydrogenated molecule whose integral mass is 100, will have a fractionally higher real mass when measured at very high resolution. In contrast a fluorinated molecule whose integral mass is 100 will tend to have a fractionally lower real mass. These differences in mass are distinguishable in a high accuracy mass analysis and two molecules with the same integral mass but different compositions will produce distinct peaks in the mass spectrum if they have different degrees of hydrogenation and fluorination. Fluorinated molecules are said to have a 'mass defect'. Since fluorinated molecules are not common in living systems, this means that a fluorinated mass label will be distinguishable in the mass spectrum even in the presence of contaminating peaks due to fragmentation of the nucleic acids or of components from buffers and other reagents as long as the nucleic acids and reagents used are not fluorinated. Incorporation of a number of units of fluorinated aryl ethers is a simple means of introducing a mass defect into the mass label. An alternative to using a separate series of mass defect groups is to replace the polymers of hydrogenated aryl-ethers with fluorinated aryl groups instead.

The poly-ether mass labels of this invention may have a variety of reactive functionalities introduced at the 'handle' position shown in the formulae of the first, second and third aspects of this invention.

Table 1 shows a variety of reactive functionalities that may be reacted together to generate a covalent linkage between two entities. Any of the functionalities listed below could be introduced at the handle position of a poly-ether mass label to permit the mass label to be readily attached to a nucleic acid or other molecule of interest. A reactive functionality could be used to introduce a further linking group with a further reactive functionality if that is desired. The table below is not in any way exhaustive and the present invention is not limited to the use of such functionalities.

TABLE I

| Functionality 1 | Functionality 2 | Resultant Linking Group |
|---|---|---|
| $R_1$—$NH_2$ | $R_2$—COOH | $R_1$—NH—CO—$R_2$ |
| $R_1$—$NH_2$ | $R_2$—NCO | $R_1$—NH—CO—NH—$R_2$ |
| $R_1$—$NH_2$ | $R_2$—NCS | $R_1$—NH—CS—NH—$R_2$ |
| $R_1$—$NH_2$ | $R_2$—CHO | $R_1$—NH—$CH_2$—$R_2$ |
| $R_1$—$NH_2$ | $R_2$—$SO_2Cl$ | $R_1$—NH—$SO_2$—$R_2$ |
| $R_1$—$NH_2$ | $R_2$—CH=$CH_2$ | $R_1$—NH—CH($CH_2$)—$R_2$ |
| $R_1$—$NH_2$ | $R_2$—CO—O—N(succinimide) | $R_1$—NH—CO—$R_2$ |
| $R_1$—OH | phosphoramidite ($R_2$—O—P(N(iPr)$_2$)—O—$CH_2CH_2$CN) | $R_1$—O—P(=O)(OH)—O—$R_2$ |
| $R_1$—C≡CH | $R_2$—X (X is Cl, Br, I) | $R_1$—C≡C—$R_2$ |
| $R_1$—epoxide | $R_2$—OH (or $R_2$—SH) | $R_1$—CH(OH)—$CH_2$—O—$R_2$ |
| $R_1$—epoxide | $R_2$—$NH_2$ | $R_1$—CH(OH)—$CH_2$—NH—$R_2$ |

It should be noted that some of the reactive functionalities above or their resultant linking groups might have to be protected prior to introduction into an oligonucleotide synthesiser. Preferably unprotected ester and thioesters, amine and amide bonds are to be avoided, as these are not stable during certain steps that take place in an oligonucleotide synthesiser. A wide variety of protective groups are known in the art to protect linkages from unwanted side reactions.

Assorted linker groups may be introduced between a poly-ether mass label of this invention and its covalently attached analyte molecule, e.g. a nucleic acid. A variety of linkers are known in the art which may be used to link two additional molecules to each other.

Oligo- or poly-ethylene glycols or their derivatives are widely used as linkers (Maskos, U. & Southern, E. M. Nucleic Acids Research 20:1679–1684, 1992). Succinic acid based linkages are also widely used although these are less preferred as they are generally base labile and are thus incompatible with the base mediated deprotection steps used in a number of oligonucleotide synthesisers.

Propargylic alcohol is a bifunctional linker that produces a linkage that is stable under the conditions of oligonucleotide synthesis and is a preferred linker for use with this invention. Similarly 6-aminohexanol is a useful bifunctional reagent to link appropriately functionalised molecules and is also a preferred linker. Another preferred bifunctional linker is a di-ynyl compound.

A variety of cleavable linker groups are known in the art and may be used in conjunction with the poly-ether mass labels of this invention. Photocleavable linkers are well known in the art. Ortho-nitrobenzyl groups are well known in the art as photocleavable linkers particularly 2-nitrobenzyl esters and 2-nitrobenzylamines, which at the benzylamine bond. For a review on cleavable linkers see Lloyd-Williams et al., Tetrahedron 49:11065–11133, 1993. This covers a variety of photocleavable and chemically cleavable linkers.

In, the present invention linkers are preferably used which have the following formula:

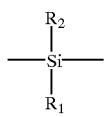

wherein $R_1$ and $R_2$ are substantially selected such that when the compound reacts with an electron donating moiety, either N or M cleaves from the Si atom in preference to $R_1$ and $R_2$.

Various substituents may be introduced at the positions $R_1$ and $R_2$ including fluorine, chlorine and other halogens, methyl, ethyl and other alkyl groups. Phenyl groups may also be appropriate. Preferably substituents at $R_1$ and $R_2$ should be stable during synthesis of the mass marker, during incorporation of the mass label into an oligonucleotide in an automated synthesiser and under mass spectrometry. A wide variety of groups will have these properties and may be incorporated into the linker at these positions. It may also be desirable to choose substituents which change the solubility of the linker and alter the rigidity of the linker.

The above cleavable linker used in this invention may be cleaved in the ion source of a mass spectrometer by ammonia. However, this aspect of the present invention is not limited to the use of ammonia. Most amines should be capable of separating the mass marker from its cognate oligonucleotide and it is also envisaged that other nucleophiles might be used.

In the present invention, alternative linkers may be used which have the following formula:

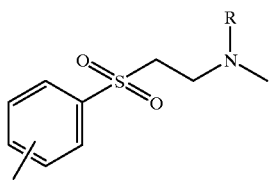

wherein R is an electron withdrawing substituent.

These linkers are advantageous in that they are thermally cleavable under mild conditions. Accordingly the mass markers can be readily cleaved from a molecule of interest within the mass spectrometer itself.

Appropriate substituents that may be introduced at the R position include hydrogen, fluorine, chlorine and other halogens. Any group that is stable and which has an electron withdrawing effect is appropriate for substitution at R, such as a trifluoroacetate group. Preferably substituents at R should be stable during synthesis of the mass marker, during incorporation of the mass label into an oligonucleotide in an automated synthesiser and under mass spectrometry, such as mesylate or tosylate groups.

The linkers used in the present invention may comprise a plurality of the above-discussed cleavable groups in the same liner (preferably in series). Thus a single linker may comprise thermally cleavable, photocleavable and/or chemically cleavable groups. These linkers are advantageous, since they are not limited to a specific method of cleavage.

The mass marker used in the compounds and methods of the present invention preferably comprises a metal ion-binding moiety. The mass marker thus achieves preferential ionisation over background material through the binding of a metal ion, effectively pre-ionising the label prior to mass spectrometry.

This ion-binding feature also ensures that there is no competition for ionisation between labels as it is relatively trivial to ensure that there are sufficient metal ions in the buffers that are used in the analytical protocols preceding mass spectrometry.

Preferred metal ions are monovalent divalent or trivalent. It is also preferred that the metal ions belong to groups IA, IIA or IIIA of the periodic table. Exemplary metal ions include $Li^+$, $Na^+$, $K^+$, $Mg^{2+}$, $Sr^{2+}$, $Ba^{2+}$, and $Al^{3+}$.

By pre-ionising the mass markers used in this invention, very gentle ionisation conditions can be used in the mass spectrometer reducing the ionisation of contaminating material. In this way the signal to noise ratio of mass spectrometry analysis steps is greatly improved.

There are a variety of molecules that are well known in the art which bind metal ions and which are appropriate for use in mass markers. Typical molecules include porphyrins, crown ethers, hexahistidine and a variety of bidentate ligands used to chelate metal ions in solution such as EDTA (Ethylenediaminetetraacetic acid). Preferred metal ion chelating groups will bind monovalent ions although entities which bind divalent ions such as EDTA could be employed with this invention.

Ion binding molecules typically have a series of nucleophilic groups in positions on the molecule where they can co-ordinate a metal ion. It is well known in the are that ion-binding molecules can be tuned to bind specifically to particular ions by altering the spacing and co-ordination of nucleophilic groups within the chelating entity.

Crown ethers are favoured for use with this invention as ethers are generally relatively fragmentation resistant and are moderately soluble. Furthermore their structures can be relatively easily "tuned" to bind certain metal ions with high specificity.

Methods of synthesis of oligonucleotides are well known in the art. The following are appropriate textbooks.

Gait, M. J. editor, "Oligonucleotide Synthesis: A Practical Approach", IRL Press, Oxford, 1990.

Eckstein, editor, "Oligonucleotides and Analogues: A Practical Approach", IRL Press, Oxford, 1991

Mass labels and their linkers can be attached to a nucleic acid molecule at a number of locations in the nucleic acid. For conventional solid phase synthesisers the 5' hydroxyl of the sugar is the easiest to derivitise. Other favoured positions for modifications are on the base at the 5' position in the pyrimidines and the 7' and 8' positions in the purines. These would be the preferred positions to attach cleavable mass labels and non-cleavable mass labels.

The 2' position on the sugar is accessible for mass modifications but is more appropriate for small mass modifications that are not to be removed.

The phosphate linkage in natural nucleic acids can be modified to a considerable degree as well, including covalent attachment of mass labels.

Depending on the application, one might wish to use modified nucleic acids containing a number of different analogues whose behaviour is modified over natural nucleic acids particularly with respect to hybridisation properties. This is particularly important when groups of hybridisation probe are used simultaneously as a multiplexed reaction using many mass labelled probes. It may be desirable to modify the hybridisation behaviour of a group of probes so that the melting temperature of correctly hybridised probes are very close or at least above some threshold. Preferably the melting temperature of incorrectly hybridised probes will fall below this threshold. This allows groups of probes to be used simultaneously whilst ensuring the stringency of hybridisation reactions. Other modifications might include the use of analogues of DNA that are fragmentation resistant in a mass spectrometer or which are resistant to degradation by enzymes.

There are major differences between the stability of short oligonucleotide duplexes containing all Watson-Crick base pairs. For example, duplexes comprising only adenine and thymine are unstable relative to duplexes containing only guanine and cytosine. These differences in stability can present problems when trying to hybridise mixtures of short oligonucleotides to a target RNA. Low temperatures are needed to hybridise A-T rich sequences but at these temperatures G-C rich sequences will hybridise to sequences that are not fully complementary. This means that some mismatches may happen and specificity can be lost for the G-C rich sequences. At higher temperatures G-C rich sequences will hybridise specifically but A-T rich sequences will not hybridise.

In order to normalise these effects modifications can be made to nucleic acids. Modifications fall into three broad categories: Base modifications, Backbone modifications and Sugar modifications.

Numerous modifications can be made to the standard Watson-Crick bases. The following are examples of modifications that should normalise base pairing energies to some extent but they are not limiting:

The adenine analogue 2,6-diaminopurine forms three hydrogen bonds to thymine rather than two and therefore forms more stable base pairs.

The thymine analogue 5-propynyl dU forms more stable base pairs with adenine.

The guanine analogue hypoxanthine forms two hydrogen bonds with cytosine rather than three and therefore forms less stable base pairs.

These and other possible modifications should make it possible to compress the temperature range at which short oligonucleotides can hybridise specifically to their complementary sequences.

Nucleotides may be readily modified in the phosphate moiety. Under certain conditions, such as low salt concentration, analogues such as methylphosphonates, tri-esters and phosphoramidates have been shown to increase duplex stability. Such modifications may also have increased nuclease resistance. Further phosphate modifications include phosphodithirates and boranophosphates, each of which increases the stability of oligonucleotide against exonucleases.

Isosteric replacement of phosphorus by sulphur gives nuclease resistant ONs (J. F. Milligan et al., J. Med. Chem. 36(14), 1923—1937, 1993.). Replacement by carbon at either phosphorus or linking oxygen is also a further possibility.

Various modifications to the 2' position in the sugar moiety may be made (C. J. Guinosso et. al., Nucleosides Nucleotides 10, 159–262, 1991; M. Carmo-Fonseca et al., EMBO J. 7, 1863–1873, 1991.). The sugar may be replaced by a different sugar such as hexose or the entire sugar phosphate backbone can be entirely replaced by a novel structure such as in peptide nucleric acids (PNA). For a discussion see P. E. Nielsen, Annu. Rev. Biophys. Biomol. Struct. 24, 167–183, 1995). PNA forms duplexes of the highest thermal stability of any analogues so far discovered and is moderately fragmentation resistant in a mass spectrometer.

The essential features of a mass spectrometer are as follows Inlet System→Ion Source→Mass Analyser→Ion Detector→Data Capture System For the purposes of analysing biomolecules, which for this application are mass labelled nucleic acids, the inlet system and ion source are particularly important features of the mass spectrometer. Other features of importance for the purposes of biological analysis are the sensitivity of the mass analyser/detector arrangements and their ability to quantify analyte molecules. Some favourable mass analysers are discussed in PCT/GB98/00127.

For many biological mass spectrometry applications so called 'soft' ionisation techniques are used. These allow large molecules such as proteins and nucleic acids to be ionised essentially intact. The liquid phase techniques allow large biomolecules to enter the mass spectrometer in solutions with mild pH and at low concentrations. A number of techniques are ideal for use with this invention including but not limited to Electrospray Ionisation (ESI), Thermospray Ionisation, Fast Atom Bombardment and Matrix Assisted Laser Desorption Ionisation (MALDI).

Electrospray Ionisation

Electrospray ionisation requires that the dilute solution of biomolecule be "nebulised" into the ion source of a mass spectrometer, i.e. injected as a fine spray. The solution is, for example, sprayed from the tip of a needle in a stream of dry nitrogen and an electrostatic field. ESI sources generally operate at ambient temperature and pressure. The mechanism of ionisation is not fully understood but is thought to work broadly as follows. In the stream of nitrogen the solvent is evaporated. With a small droplet, this results in concentration of the biomolecule. Given that most biomolecules have a net charge this increases the electrostatic repulsion of the dissolved protein. As evaporation continues this repulsion ultimately becomes greater than the surface tension of the droplet and the droplet 'explodes' into smaller droplets. The electrostatic field helps to further overcome the surface tension of the droplets and assists in the spraying process. The evaporation continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber through a pair of electrodes. The potential difference across these electrodes determines whether positive or negative ions pass into the mass analyser and also the energy with which these ions enter the mass spectrometer. This is of significance when considering fragmentation of ions in the mass spectrometer.

The more energy imparted to a population of ions the more likely it is that fragmentation will occur through collision of analyte molecules with the bath gas present in the source. By adjusting the accelerating voltage used to accelerate ions from the ionisation chamber one can control the fragmentation of ions and, to some extent, the degree of ionisation. For the purposes of this invention fragmentation and ionisation of nucleic acids and background contaminants is preferably voided. ESI is advantageous for this purpose in that fragmentation can be greatly reduced by accelerating ions through the ion source with a relatively low cone voltage.

Thermospray Ionisation

Thermospray ionisation is an older technique related to ESI which also "nebulises" a dilute solution of the analyte biomolecule into the ion source of a mass spectrometer. In thermospray, however, the solution is sprayed from the tip of a heated capillary into a vacuum without an electrostatic field. The low pressure and heating of the analyte solution promotes solvent evaporation and ionisation. The process does produce charged droplets but tends to produce equal numbers of oppositely charged droplets, i.e. no net charge. The mechanism of solvent evaporation and ionisation is thought to work in a manner similar to ESI. The thermal nature of the process means that, in general, more energy is imparted to analyte ions and so there tends to be more fragmentation with thermospray methods. Thermospray also tends to produce singly charged ions in contrast to ESI which produces a variety of multiply charged ions.

Matrix Assisted Laser Desorption Ionisation (MALDI)

MALDI requires that the biomolecule solution be embedded in a large molar excess of a photo-excitable 'matrix'. The application of laser light of the appropriate frequency (266 nm beam for nicotinic acid) results in the excitation of the matrix which in turn leads to excitation and ionisation of the embedded biomolecule. This technique imparts a significant quantity of translational energy to ions, but tends not to induce excessive fragmentation despite this. Accelerating voltages can again be used to control fragmentation with this technique though.

MALDI techniques can be supported in two ways. One can embed mass labelled DNA in a MALDI matrix, where the labels themselves are not specifically excitable by laser or one can construct labels that contain the necessary groups to allow laser energisation. The latter approach means the labels do not need to be embedded in a matrix before performing mass spectrometry. Such groups include nicotinic, sinapinic or cinnamic acid moieties. MALDI based cleavage of labels would probably be most effective with a photocleavable linker as this would avoid a cleavage step prior to performing MALDI mass spectrometry. The various excitable ionisation agents have different excitation frequencies so that a different frequency can be chosen to trigger ionisation from that used to cleave the photocleavable linker. These excitable moieties are easily derivitised using standard synthetic techniques in organic chemistry so labels with multiple masses can be constructed in a combinatorial manner.

Fast Atom Bombardment

Fast Atom Bombardment (FAB) has come to describe a number of techniques for vaporising and ionising relatively involatile molecules. The essential principal of these techniques is that samples are desorbed from surfaces by collision of the sample with accelerated atoms or ions, usually xenon atoms or caesium ions. The samples may be coated into a solid surface as for MALDI but without the requirement of complex matrices. These techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment. FAB is known to fetch pre-ionised material from the frit surface with high efficiency and is thus likely to be another highly favoured inlet and ionisation procedure.

EXAMPLE 1

Synthesis of a trimeric poly-ether

Figure 3:
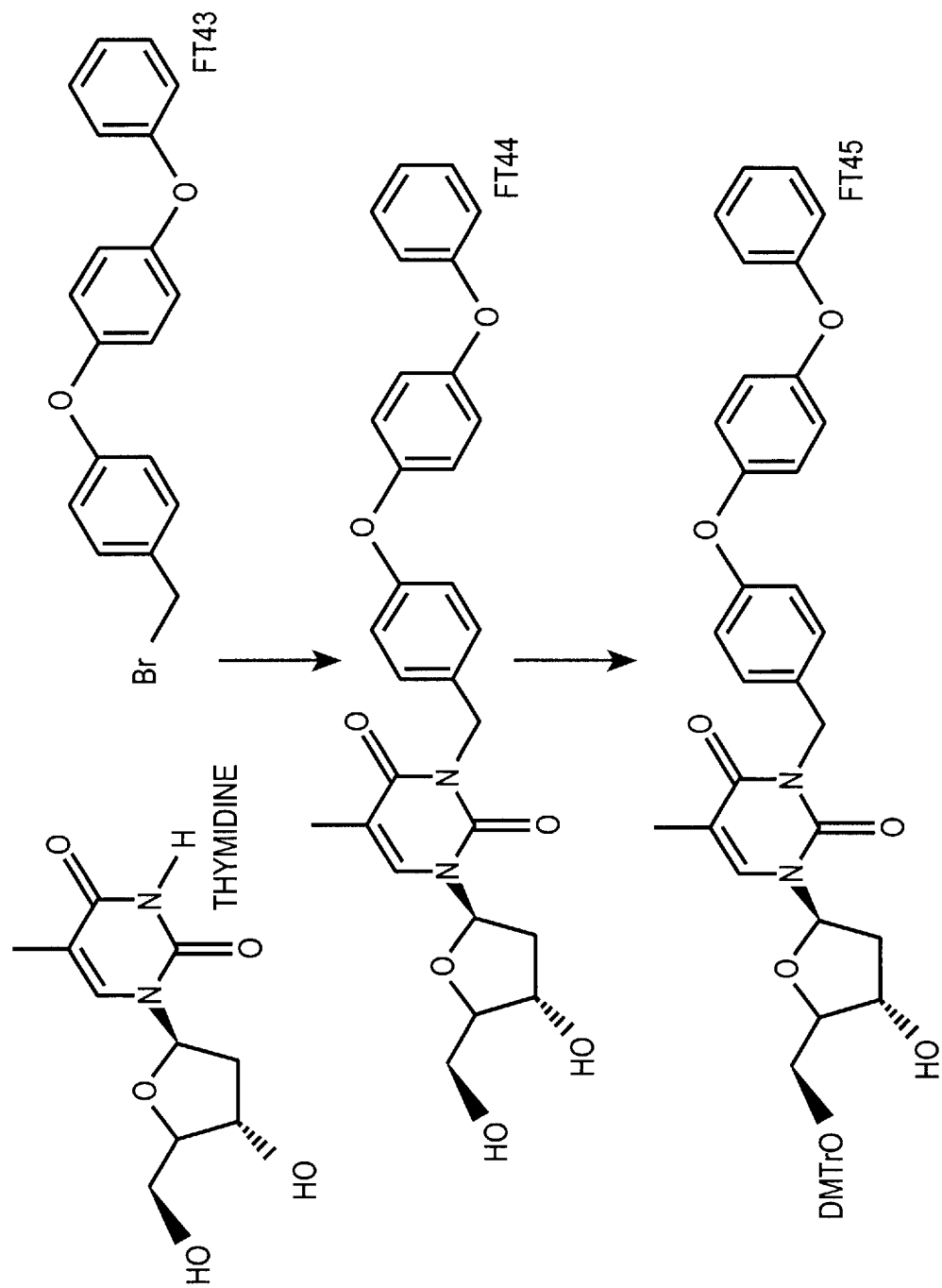
FIG. 3 shows the attachment of a trimeric poly-ether to a nucleoside which is subsequently protected at the 5' hydroxyl of the sugar.

A trimeric poly-ether was synthesised using commercially available intermediates. The trimeric poly-ether was reacted to form a number of trimers with different reactive handles at one terminus of the trimer. (see FIG. 2) The first trimeric intermediate is referred to as FT77. This was converted to FT36 which has a hydroxyl group at one terminus. This was then reacted to introduce a bromide entity (FT43). This intermediate can be attached directly to a nucleoside, FT45 (see FIG. 3) or can be reacted with a bifunctional linker, propargylic alcohol, to produce a further intermediate, FT52, which may be attached to a nucleoside, FT56 (see FIG. 4).

Synthesis of FT77

A suspension of a 60% dispersion of sodium hydride in mineral oil (1.6 g, 40 mmol) in dry pyridine (20 ml) was treated dropwise with a solution of 4-phenoxyphenol in dry pyridine (20 ml). After evolution of hydrogen had finished the reaction mixture was treated with anhydrous copper(I) chloride (1.98 g, 20 mmol) and stirred for 15 min at room temperature. Subsequently, a solution of methyl 4-bromobenzoate (4.30 g, 20 mmol) in dry pyridine (10 ml) was added. The reaction mixture was refluxed for two hours, cooled down to room temperature, diluted with toluene (100 ml) and filtered. The filtrate was evaporated to dryness under reduced pressure followed by co-evaporation with toluene (2×100 ml). The residue was dissolved in diethyl ether (150 ml) and filtered. The filtrate was washed in sequence with 2 N aqueous HCl, water, 1 N aqueous KOH (5×), 2 N aqueous HCl, and water. The organic phase was dried with sodium sulphate and evaporated to dryness under reduced pressure. The residue was adsorbed on silica gel (0.2–0.5 mm, 15 g) and purified by flash chromatography on silica gel with n-hexane/toluene (75:25 ) to yield FT77 (3.9 g, 61%).

Confirmation of Identity of FT77 Product

M.p. 111–113° C.

$^1$H NMR (CDCl$_3$) 3.90 (s, 32 H), 6.96–7.05 (m, 8 H), 7.11 (m, 1 H), 7.31–7.38 (m, 2 H), 7.98–8.03 (m, 2 H); $^{13}$C NMR (CDCl$_3$) 51.90, 116.92, 118.72, 120.44, 212.61, 123.42, 124.51, 129.90, 131.79, 151.11, 154.02, 157.56, 162.34, 166.72;

Mass spectrometry of the compound using Electron Impact Ionisation to ionise the compound gave a molecular ion peak with an m/z of 320 (M$^+$).

Synthesis of FT36

A suspension of lithium aluminum hydride (600 mg, 16 mmol) in dry tetrahydrofuran (10 ml) was cooled to 0° C. and treated with a solution of FT77 (2.0 g, 6.25 mmol) in tetrahydrofuran (10 ml). After 10 min the cooling bath was removed and stirring was continued for 40 min. The reaction mixture was treated dropwise with ethyl acetate (5 ml) and then with 10% aqueous citric acid (5 ml). The reaction mixture was filtered through Celite. The filtrate was diluted with ethyl acetate and washed with 10% aqueous citric acid, water (2×) and dried with sodium sulphate. Evaporation of the solvent under reduced pressure furnished FT36 (1.80 g, 99%).

Confirmation of Identity of FT36 Product

M.p. 116–118° C. (ethyl acetate/n-hexane).

$^1$H NMR (CDCl$_3$) 1.61 (br s, 1 H), 4.67 (s, 2 H), 6.98–7.50 (m, 8 H), 7.09 (m, 1 H), 7.30–7.37 (m, 4 H);

Mass spectrometry of the compound using Fast Atom Bombardment to ionise the compound gave a molecular ion peak with an m/z of 292 (M$^+$).

Synthesis of FT43

A solution of FT36 (730 mg, 2.5 mmol) in dry dichloromethane (20 ml) was treated with bromotrimethylsilane (1 ml, 7.5 mmol) and stirred for 30 min at room temperature. The reaction mixture was washed with water (3×). The organic phase was dried with sodium sulphate and evaporated to dryness under reduced pressure to afford pure FT43 (802 mg, 90%).

Confirmation of Identity of FT43 Product

M.p. 90–91° C. (diethyl ether/n-hexane); Calculated Atomic Composition: C 64.24, H 4.26; Measured Composition: C 63.62, H 4.18.

$^1$H NMR (CDCl$_3$) 4.50 (s, 2 H), 6.92–7.03 (m, 8 H), 7.09 (m, 1 H), 7.30–7.37 (m, 4 H); $^{13}$C NMR (CDCl$_3$) 33.27, 118.21, 118.51, 120.48, 129.93, 123.21, 129.83, 130.68, 132.30, 152.11, 153.30, 157.23, 158.21;

Mass spectrometry of the compound using Electron Impact Ionisation to ionise the compound gave a molecular ion peak with an m/z of 354/356 (M$^+$).

EXAMPLE 2

Synthesis of a mass labelled nucleoside

A mass labelled nucleoside referred to as FT44 was prepared with a poly-ether mass label attached to the 3' position of a thymidine nucleobase. (see FIG. 3)

Synthesis of FT44

A solution of thymidine (302 mg, 1.25 mmol), potassium carbonate (207 mg, 1.5 mmol) and FT43 (497 mg, 1.4 mmol) in acetone/N,N-dimethylformamide (10 ml, 1:1) was stirred for 90 min at 60° C. The reaction mixture was diluted with acetone and filtered. The filtrate was evaporated to dryness by co-evaporation with toluene. The residue was purified by flash chromatography on silica gel with ethyl acetate/ethanol (97:3) to furnish FT44 (494 mg, 85%) as a colourless foam.

Confirmation of Identity of FT44 Product

Atomic Composition Calculated for C$_{29}$H$_{28}$N$_2$O$_7$ 0.5 H$_2$O; Predicted: C 66.02, H 5.54, N 5.31; Measured: C 65.80, H 5.55, N 5.31.

$^1$H NMR (CDCl$_3$) 1.94 (s, 3 H), 2.15 (d, J=4 Hz, 1H), 2.27–2.47 (m, 4 H), 3.80–4.02, 3 H), 4.59 (m, 1 H), 5.42 (s, 2 H), 6.21 (t, J=7 Hz, 1 H), 6.90–7.49 (m, 14 H).

EXAMPLE 3

Synthesis of a 'protected' mass labelled nucleoside

The mass labelled nucleoside FT44 was then reacted with a protective group to give a new compound referred to as FT45. The 5' hydroxyl group of the nucleoside was protected with a dimethoxytrityl protective group leaving the 3' hydroxyl group accessible for the addition of a 2-cyanoethyl-N,N-diisopropylchlorophosphoramidite. The phosphoramidite group will then permit the labelled base to be incorporated into an oligonucleotide in a conventional automated oligonucleotide synthesiser from Perkin Elmer Applied Biosystems. (see FIG. 3)

Synthesis of FT45

A solution of FT44 (200 mg, 0.38 mmol) in dry pyridine (3 ml) was treated with 4,4'-dimethoxytritylchloride (170 mg, 0.5 mmol) and 4-N,N-dimethylaminopyridine (10 mg). The reaction mixture was stirred for 23 hours at room temperature, then pyridine was removed by co-evaporation with toluene under reduced pressure. The residue was dissolved in dichloromethane and washed with 10% aqueous citric acid and water (2×). The organic phase was dried with sodium sulphate and evaporated to dryness under reduced pressure. Flash chromatography on silica gel with ethyl acetate/n-hexane (1:1) containing 1% of triethylamine afforded FT45 (216 mg, 69%) as a colourless foam.

Confirmation of Identity of FT45 Product

Atomic Composition Calculated for C$_{50}$H$_{46}$N$_2$O$_9$ 0.5 H$_2$O; Predicted: C, 72.54; H, 5.72. N, 3.38; Measured: C, 72.55. H, 5.51. N, 2.99.

$^1$H NMR (CDCl$_3$) 1.53 (s, 3 H), 2.27–2.40 (m, 2 H), 3.34–3.51 (m, 4 H), 3.78 (s, 6 H), 4.01 (t, J=3 Hz, 1 H), 4.55 (t, J=3 Hz, 1 H), 5.08 (d, J=2 Hz, 2 H), 6.43 (t, J=7 Hz, 1 H), 6.80–7.55 (m, 25 H);

Mass spectrometry of the compound using Fast Atom Bombardment to ionise the compound gave a molecular ion peak with an m/z of 819 [M+H]$^+$.

Synthesis of a poly-ether mass label with a linker for attachment to a nucleoside The trimeric poly-ether intermediate FT43 was reacted with propargylic alcohol to give a mass label with a linker appropriate for attachment to a nucleoside. (See FIG. 2)

Synthesis of FT52

A suspension of a 60% dispersion of sodium hydride in mineral oil (172 mg, 4.3 mmol) in tetrahydrofuran (5 ml) was treated with propargylic alcohol (252 mg, 4.5 mmol) and stirred for ten min at room temperature. Then a solution of FT43 in tetrahydrofuran (4 ml) was added followed by anhydrous potassium iodide (50 mg). The reaction mixture was stirred for 8 hours at room temperature, diluted with diethyl ether, washed with 10% aqueous citric acid and water (2×). The organic phase was dried with sodium sulphate and the solvents were removed under reduced pressure. The residue was purified by flash chromatography on silica gel with n-hexane/tert-butyl methyl ether (95:5) to yield FT52 (940 mg, 95%).

Confirmation of Identity of FT52 Product

M.p. 54–56° C. (ethanol/water); Calculated Atomic Composition: C, 79.98; H, 5.49; Measured: C, 79.58; H, 5.54.

$^1$H NMR (CDCl$_3$) 2.46 (t, J=2.5 Hz, 1H), 4.17 (d, J=2.5 Hz, 2 H), 4.57 (s, 2 H), 6.95–7.02 (m, 8 H), 7.08 (m, 1 H), 7.29–7.36 (m, 4 H); $^{13}$C NMR (CDCl$_3$) 56.97, 71.04, 74.59, 79.67, 118.31, 118.40, 120.49, 129.52, 123.10, 129.81, 129.90, 132.05, 152.76, 152.96, 157.34, 157.88;

Mass spectrometry of the compound using Electron Impact Ionisation to ionise the compound gave a molecular ion peak with an m/z of 330 (M$^+$).

EXAMPLE 4

Synthesis of a mass labelled, 'protected' nucleoside

Figure 4:
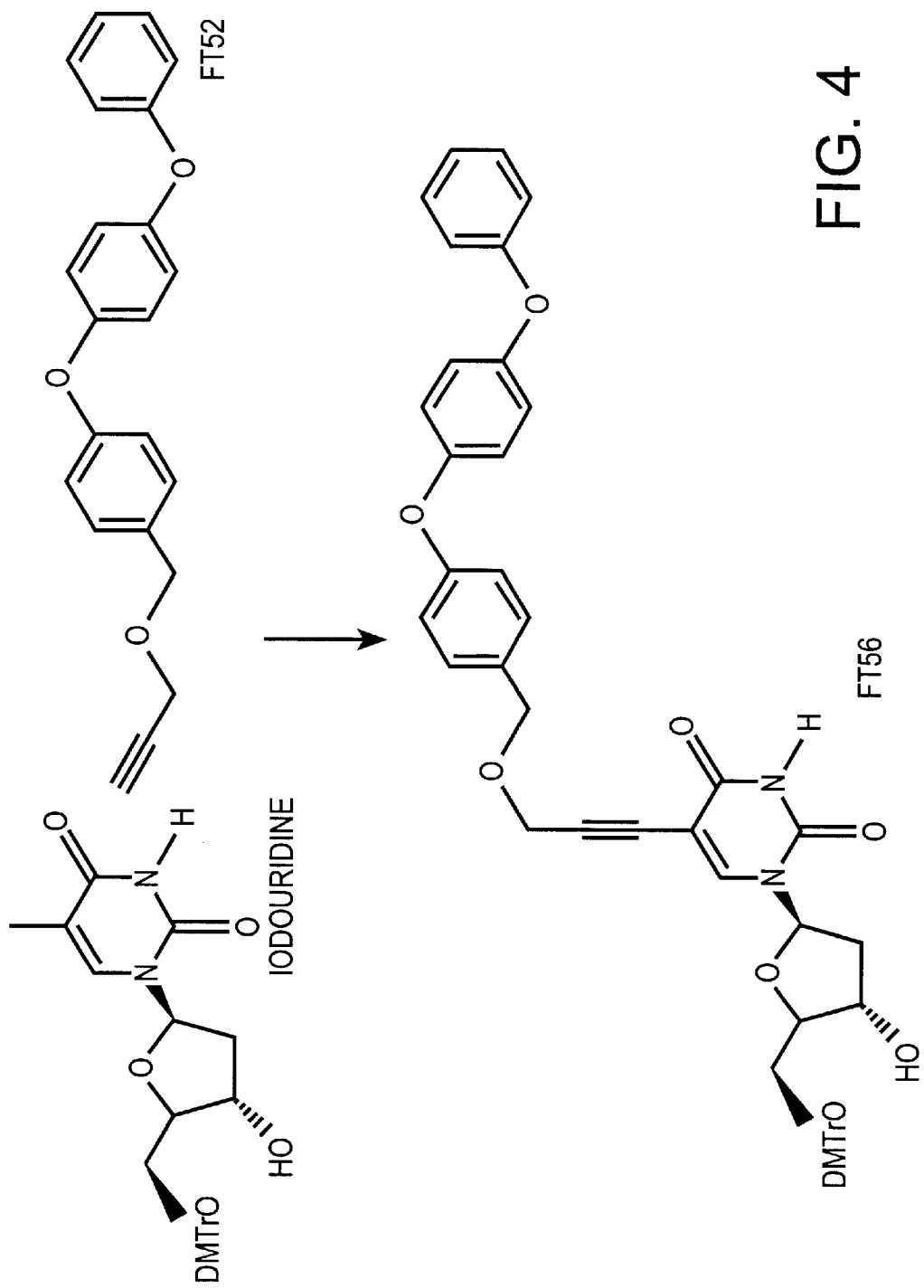
FIG. 4 shows the attachment of a trimeric poly-ether to a protected base.

A mass labelled nucleoside referred to as FT56 was prepared with a poly-ether mass label attached to the 5' position of a 5'-iodouridine nucleoside (see FIG. 4). The 5' hydroxyl group of the nucleoside was protected with a dimethoxytrityl protective group leaving the 3' hydroxyl group accessible for the addition of a 2-cyanoethyl-N,N-diisopropylchlorophosphoramidite. The phosphoramidite group will then permit the labelled based to be incorporated into an oligonucleotide in a conventional automated oligonucleotide synthesiser from Perkin Elmer Applied Biosystems. Alternatively the protected nucleoside can be converted into a nucleotide triphosphate. The mass label was attached to the base via a propargylic linker. Uridine and cytidine bases labelled at the 5' position of the base are known to be accepted by certain polymerases and can be used in labelled terminator sequencing reactions.

Synthesis of FT56

A solution of 5'-(4,4'-dimethoxytrityl)-5-iodouridine (656 mg, 1 mmol) in N,N-dimethylformamide (5 ml) was treated in sequence with FT52 (660 mg, 2 mmol), copper(I) iodide (38 mg, 0.2 mmol), triethylamine (0.7 ml, 5 mmol) and palladium(0) tetrakistriphenylphosphine (115 mg, 0.1 mmol) and stirred for 5 hours at room temperature. The solvents were removed under reduced pressure by co-evaporation with toluene. The residue was dissolved in dichloromethane and washed with a 5% aqueous solution of disodium-EDTA (2×) 10% sodium thiosulphate and water. The organic was dried with sodium sulphate and evaporated to dryness under reduced pressure. The residue was purified by flash chromatography on silica gel with dichloromethane/methanol (95:5) containing 0.5% of triethylamine and subsequently with ethyl acetate/n-hexane/EtOH/triethylamine (60:35:5:1) to yield FT56 (750 mg, 87%) as a pale yellow foam.

Confirmation of Identity of FT56 Product

Calculated Atomic Composition: C, 72.71; H, 5.40; N, 3.26; Measured Composition: C, 72.68; H, 5.45; N, 3.21.

$^1$H NMR (CDCl$_3$) 2.27 (m, 1 H), 2.49 (ddd, J=14, 7 and 3 Hz, 1 H), 3.38 (m, 2 H), 3.74 (s, 6 H), 4.03–4.10 (m, 3 H), 4.37 (s, 2 H), 4.50 (m, 1 H), 6.29 (t, J=2 Hz, 1 H), 6.80–7.43 (m, 27 H), 8.06 (s, 1 H);

Mass spectrometry of the compound using Fast Atom Bombardment to ionise the compound gave a molecular ion peak with an m/z of 858 [M+H]$^+$.

EXAMPLE 5

Synthesis of substituted poly-ether mass labels

Figure 5:
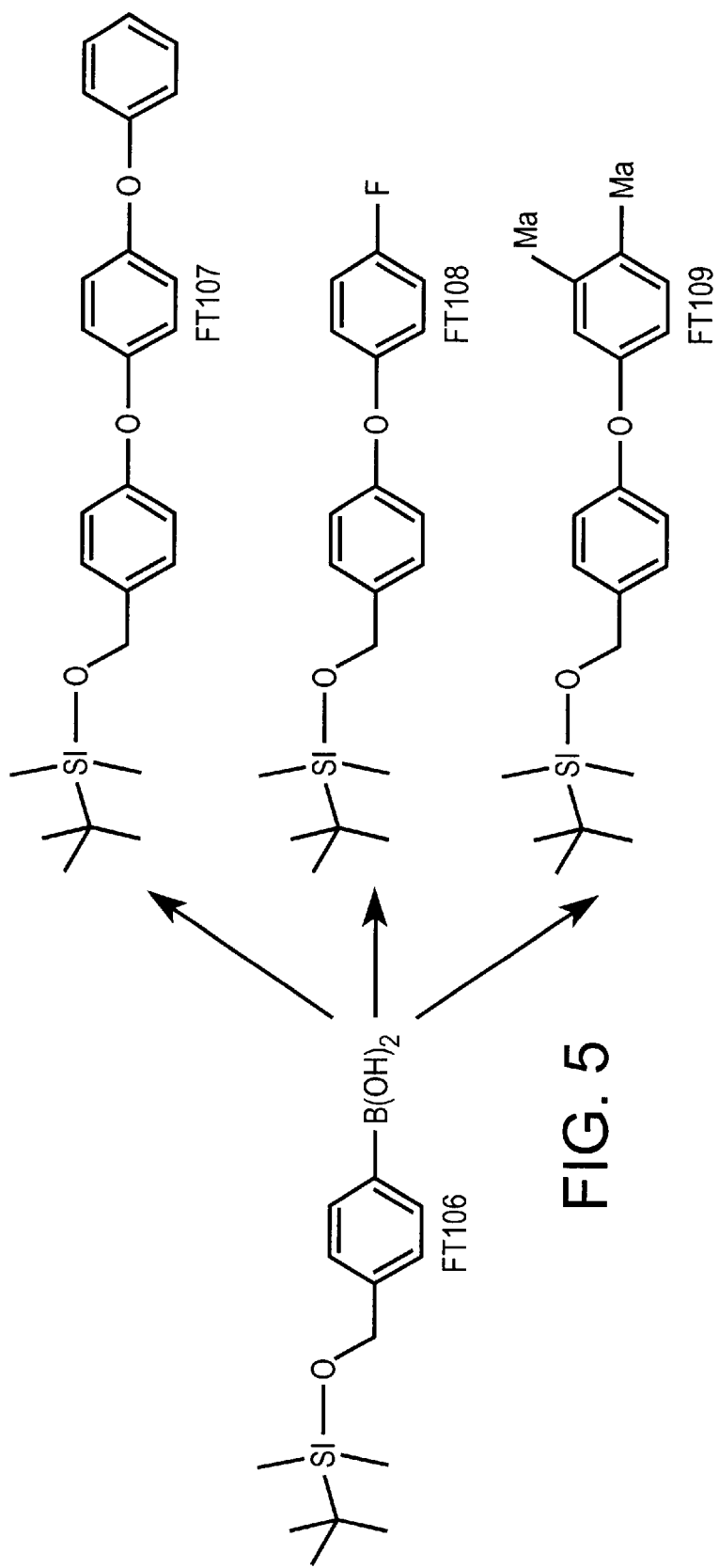
FIG. 5 shows the synthesis of three mass-modified poly-ethers.

As discussed above it is proposed to generate arrays of mass labels closely spaced in the mass spectrum by modifying a polymeric series of a poly-ether with variable mass series modifying groups. The synthesis of examples of such mass series modified groups is described below. A precursor molecule, referred to as FT106, was synthesised from which 3 different mass labels were synthesised, which are referred to as FT107, FT108 and FT109. (see FIG. 5)

Synthesis of FT106

This compound was prepared by reaction of tert-butyldimethylsilyl-4-bromobenzylalcohol with butyl lithium, followed by reaction with a trialkyl borate and subsequent acidic hydrolysis.

General procedure for FT107, FT108, FT109

Phenols used to generate mass labels:

FT107—4-phenoxyphenol

FT108—4-fluorophenol

FT109—3,4-dimethylphenol

A suspension of the corresponding phenol (0.5 mmol), anhydrous copper(II) acetate (91 mg, 0.5 mmol) boronic acid, FT106 (201 mg, 0.75 mmol) and powdered freshly activated molecular sieve 4 (100 mg) in dry dichloromethane (5 ml) was treated with dry triethylamine (252 mg, 2.5 mmol) and stirred at room temperature for two hours. The reaction mixture was filtered and the filtrate evaporated to dryness under reduced pressure. The residue was dissolved in dichloromethane and washed with a 5% aqueous solution of disodium-EDTA and water. The organic phase was dried with sodium sulphate and evaporated to dryness under reduced pressure. The residue was purified by flash chromatography on silica gel with n-hexane/toluene (4:1) to give the corresponding arylethers FT107, FT108, and FT109.

Confirmation of Identity of FT107 Products

FT107: 135 mg (66%). M.p. 67–68° C. (EtOH); Calculated Atomic Composition: C, 73.85; H, 7.44; Measured Composition: C, 73.88; H, 7.48.

$^1$H NMR (CDCl$_3$) 0.1 (s, 6 H), 0.94 (s, 9 H), 4.62 (s, 2 H), 6.96–7.09 (m, 6 H), 7.10 (m, 1 H), 7.25–8.36 (m, 6 H);

Mass spectrometry of the compound using Chemical Ionisation gave a molecular ion peak with an m/z of 406 (M$^+$).

Confirmation of Identity of FT108 Product

FT108: 110 mg (66%). Colourless oil; Calculated Atomic Composition: C, 68.64; H, 7.58; Measured Composition: 68.80; H, 7.70.

$^1$H NMR (CDCl$_3$) 0.1 (s, 6 H), 0.94 (s, 9 H), 4.61 (s, 2 H), 6.92–7.99 (m, 6 H), 7.16 (m, 2 H);

Mass spectrometry of the compound using Chemical Ionisation gave a molecular ion peak with an m/z of 332 (M$^+$) and a second major peak at m/z 350 [M+NH$_4$]$^+$.

Confirmation of Identity of FT109 Product

FT109: 84 mg (49%). Colourless oil; Calculated Atomic Composition: C, 73.63; H, 8.83; Measured Composition: C, 73.77; H, 8.88.

$^1$H NMR (CDCl$_3$) 0.1 (s, 6 H), 0.93 (s, 9 H), 2.13 (s, 6 H), 4.61 (s, 2 H), 6.73 (dd, J=9 and 2 Hz, 1 H), 6.81 (d, J=3 Hz, 1 H), 6.95 (d, J=8 Hz, 2 H), 7.07 (d, J=8 Hz, 1 H), 7.27 (d, J=4 Hz, 2 H); $^{13}$C NMR (CDCl$_3$) –4.00, 19.66, 20.18, 21.10, 65.91, 117.52, 119.63, 121.54, 128.81, 131.86, 132.66, 137.20, 139.40, 156.55, 158.07;

Mass spectrometry of the compound using Chemical Ionisation gave a molecular ion peak with an m/z of 342 (M$^+$).

EXAMPLE 6

Figure 6:
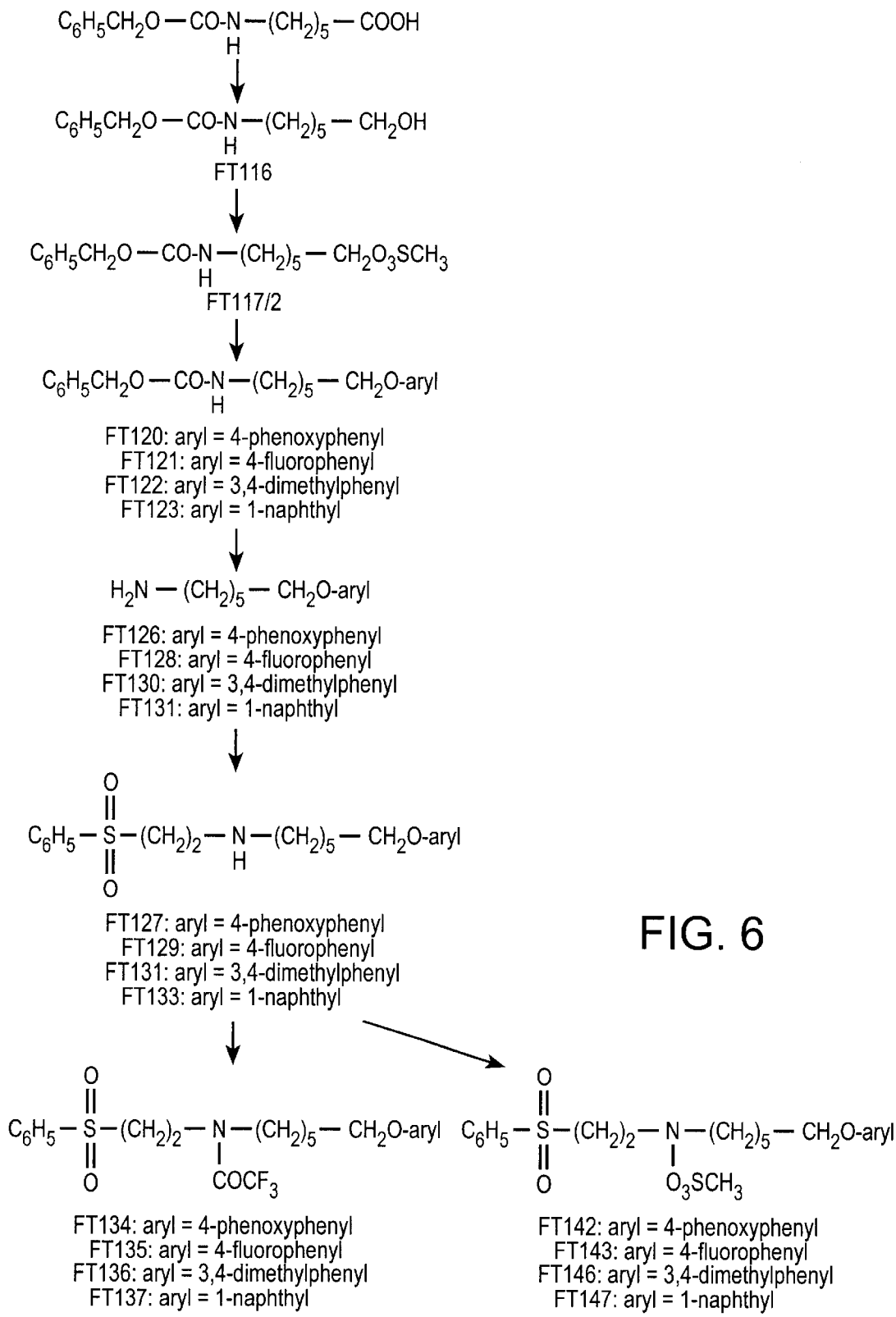
FIG. 6 shows a schematic diagram of the synthesis of a series of mass labels that are cleavable in an electrospray ion source.
Figure 7:
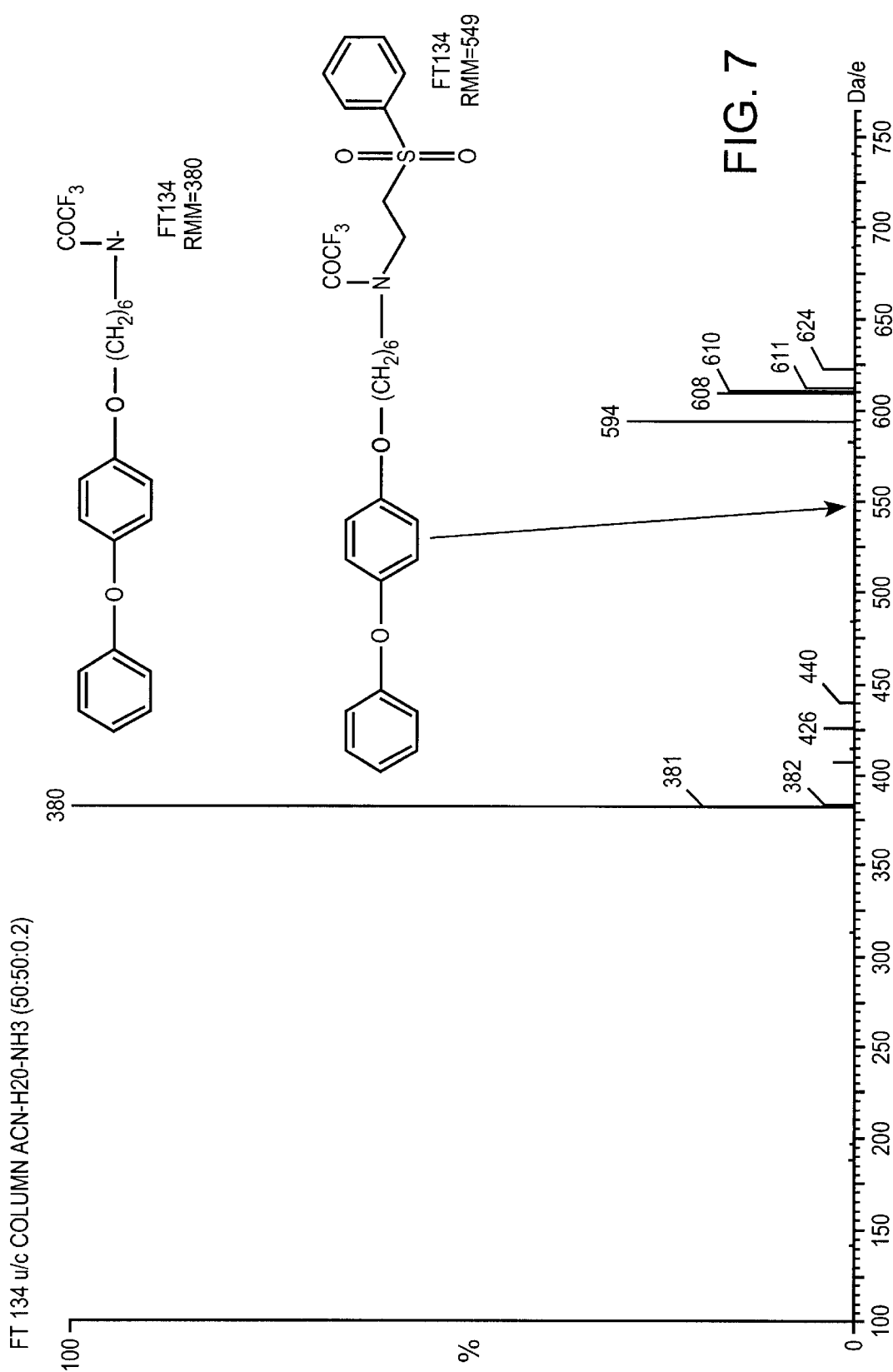
FIG. 7 shows the electrospray mass spectrum of FT134 which is an ether mass marker that is attached to a linker that is cleavable in an electrospray ion source.
Figure 8:
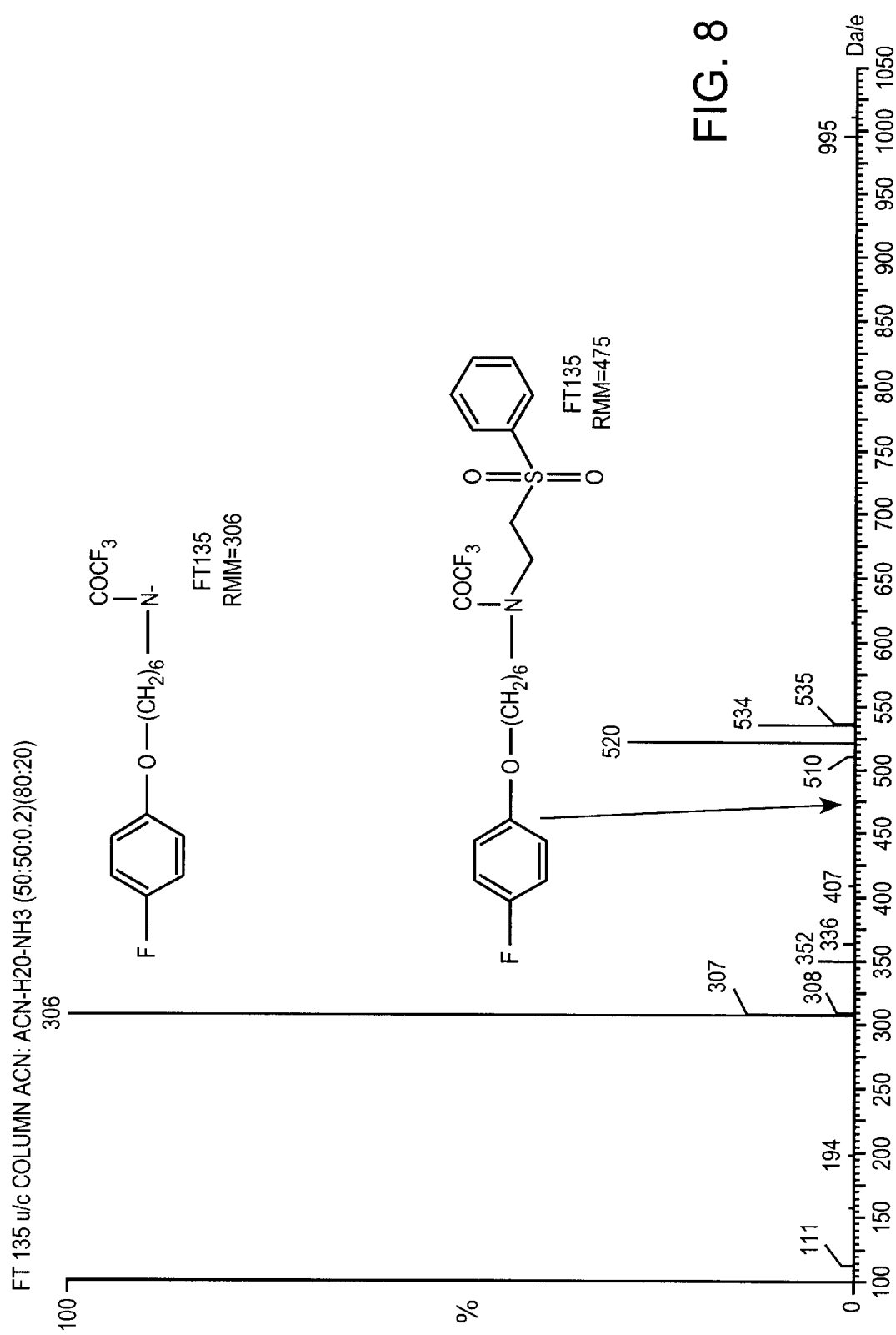
FIG. 8 shows the electrospray mass spectrum of FT135 which is an ether mass marker that is attached to a linker that is cleavable in an electrospray ion source.
Figure 9:
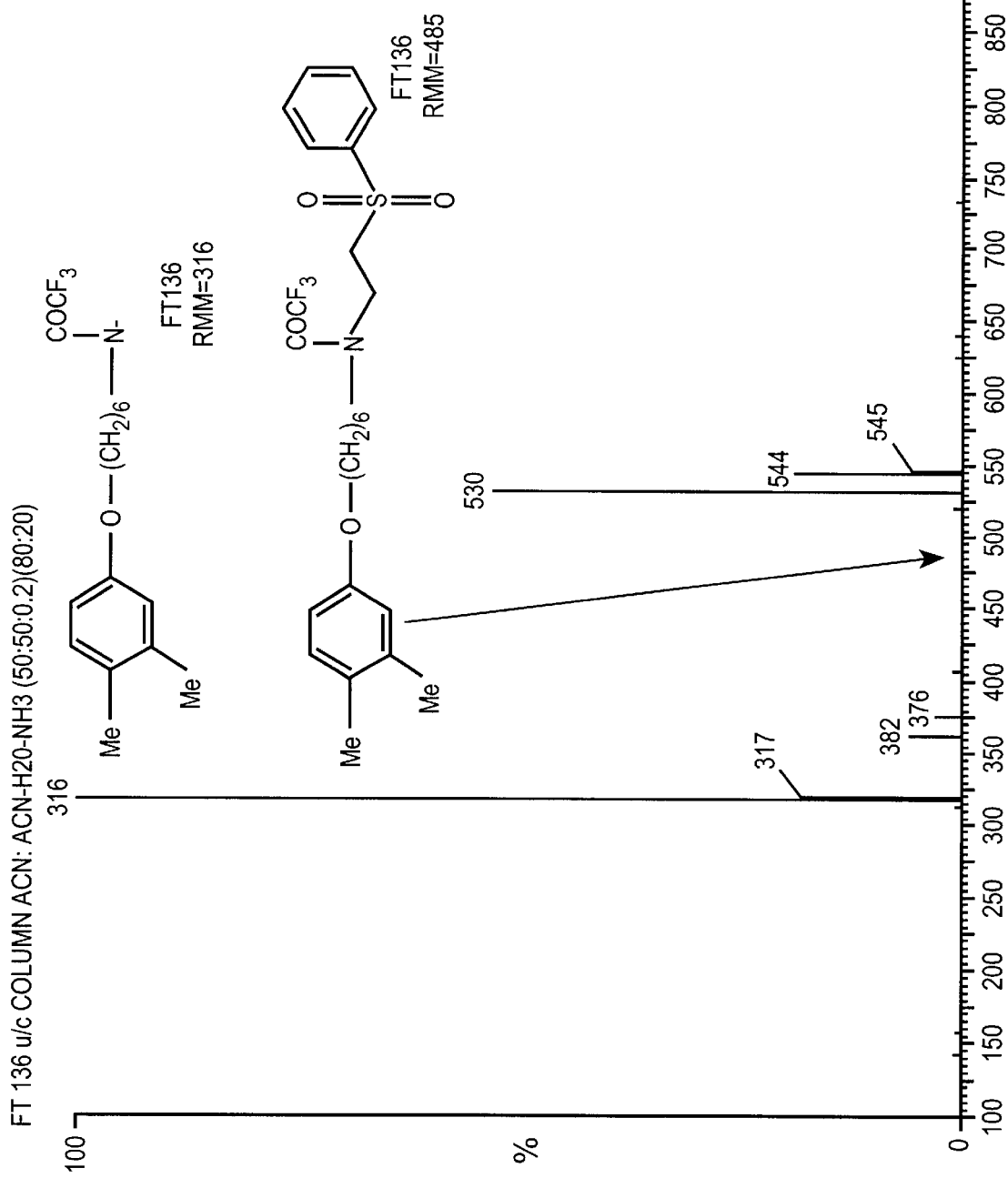
FIG. 9 shows the electrospray mass spectrum of FT136 which is an ether mass marker that is attached to a linker that is cleavable in an electrospray ion source.
Figure 10:
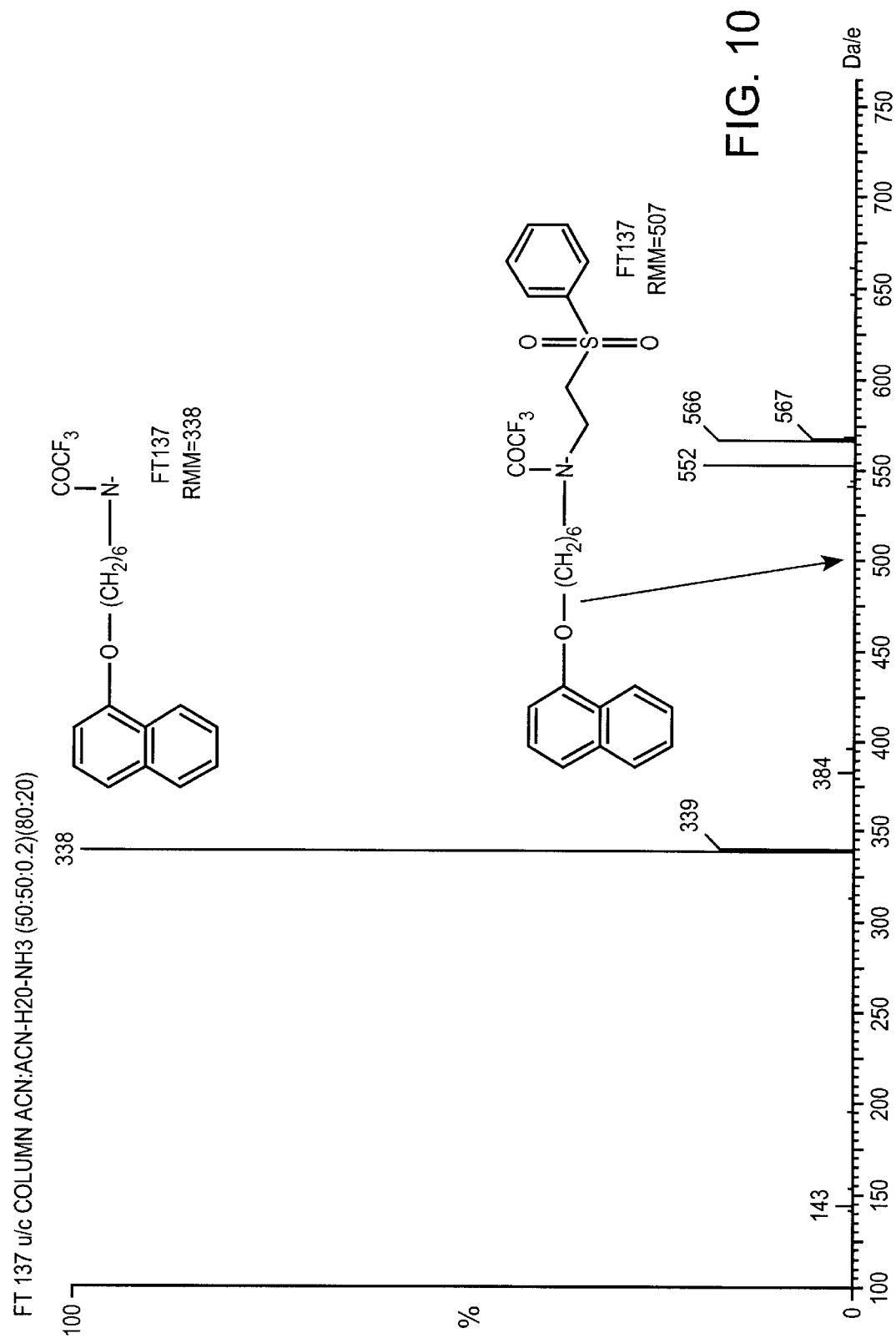
FIG. 10 shows the electrospray mass spectrum of FT137 which is an ether mass marker that is attached to a linker that is cleavable in an electrospray ion source.
Figure 11:
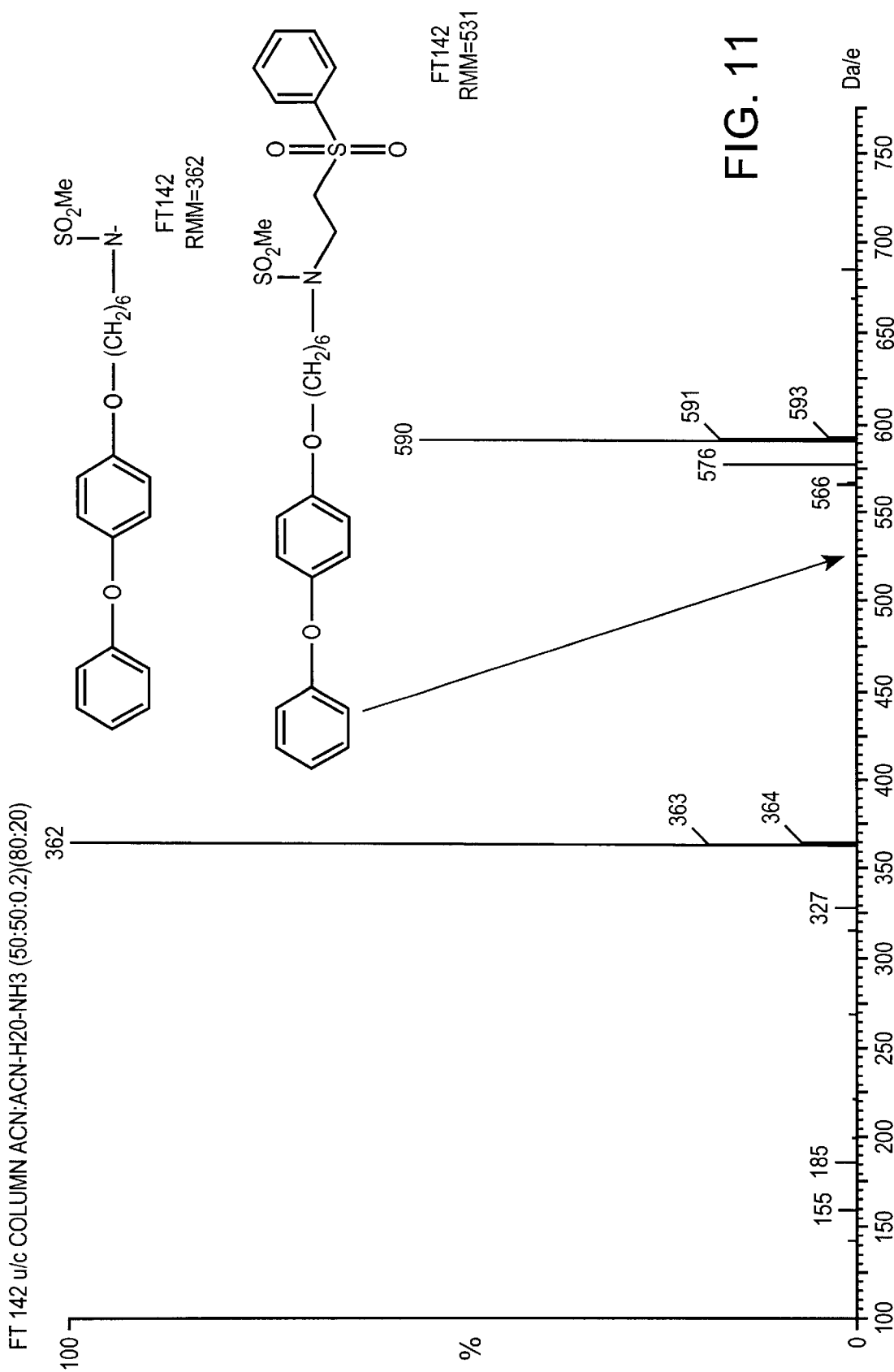
FIG. 11 shows the electrospray mass spectrum of FT142 which is an ether mass marker that is attached to a linker that is cleavable in an electrospray ion source.
Figure 12:
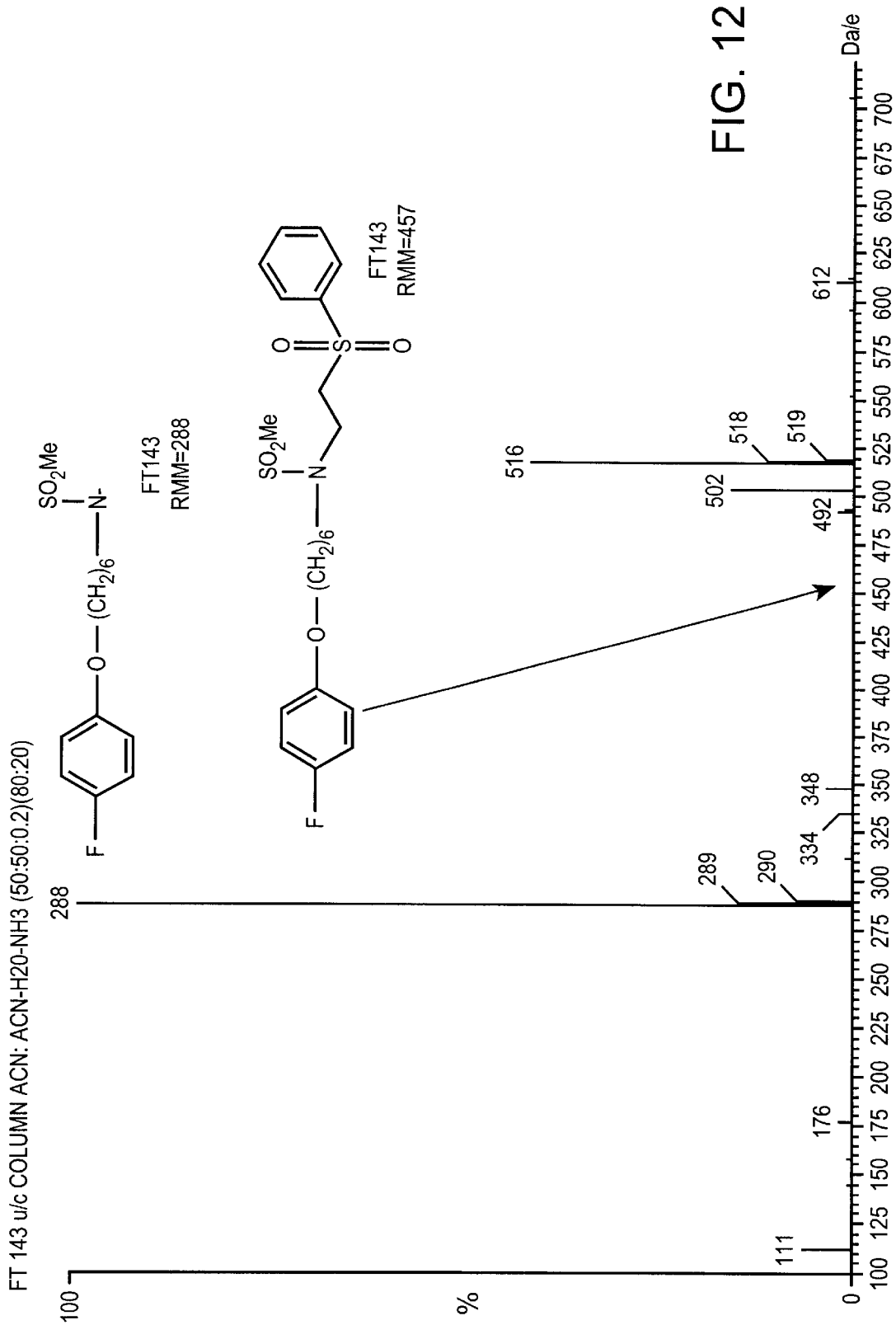
FIG. 12 shows the electrospray mass spectrum of FT143 which is an ether mass marker that is attached to a linker that is cleavable in an electrospray ion source.
Figure 13:
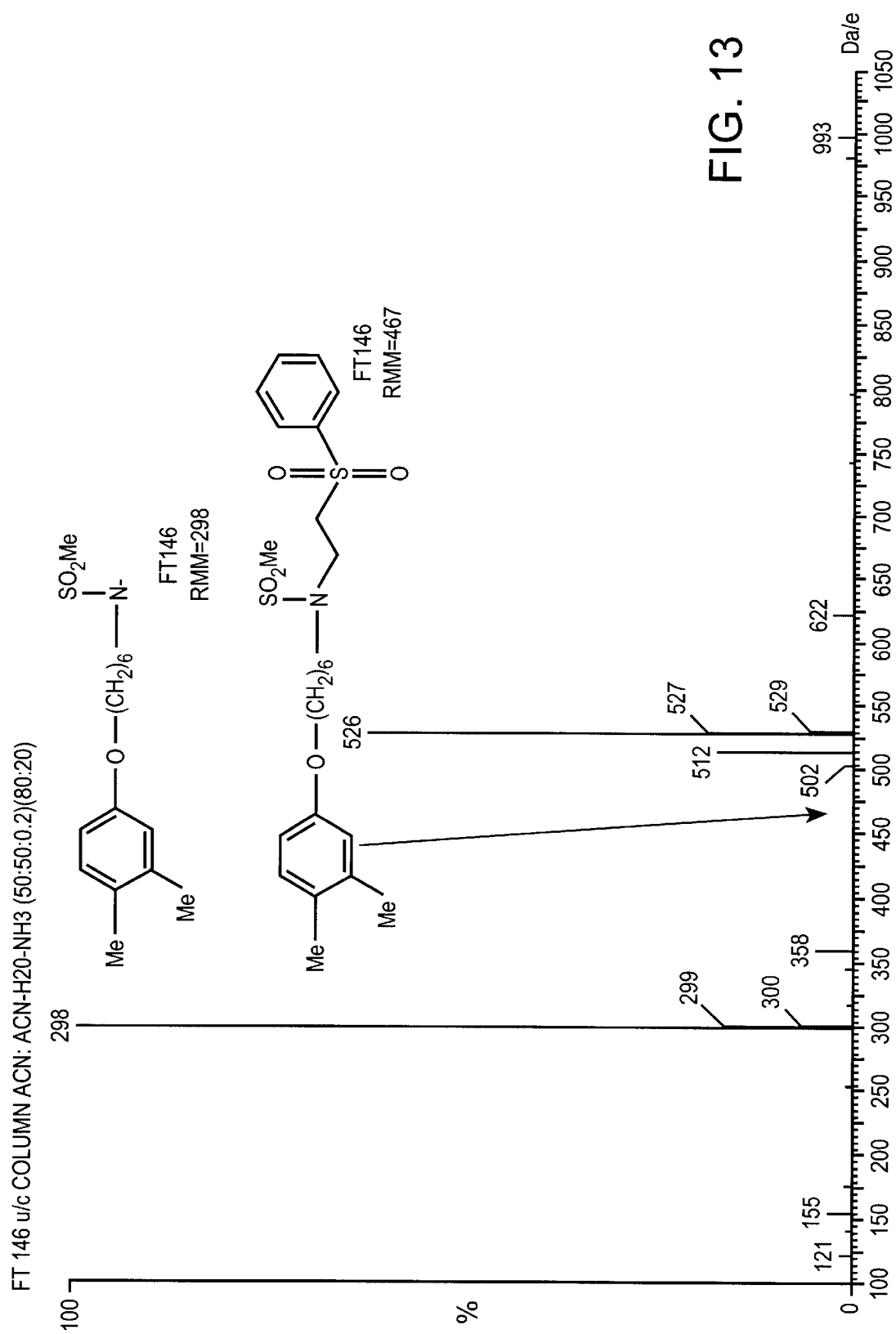
FIG. 13 shows the electrospray mass spectrum of FT146 which is an ether mass marker that is attached to a linker that is cleavable in an electrospray ion source.
Figure 14:
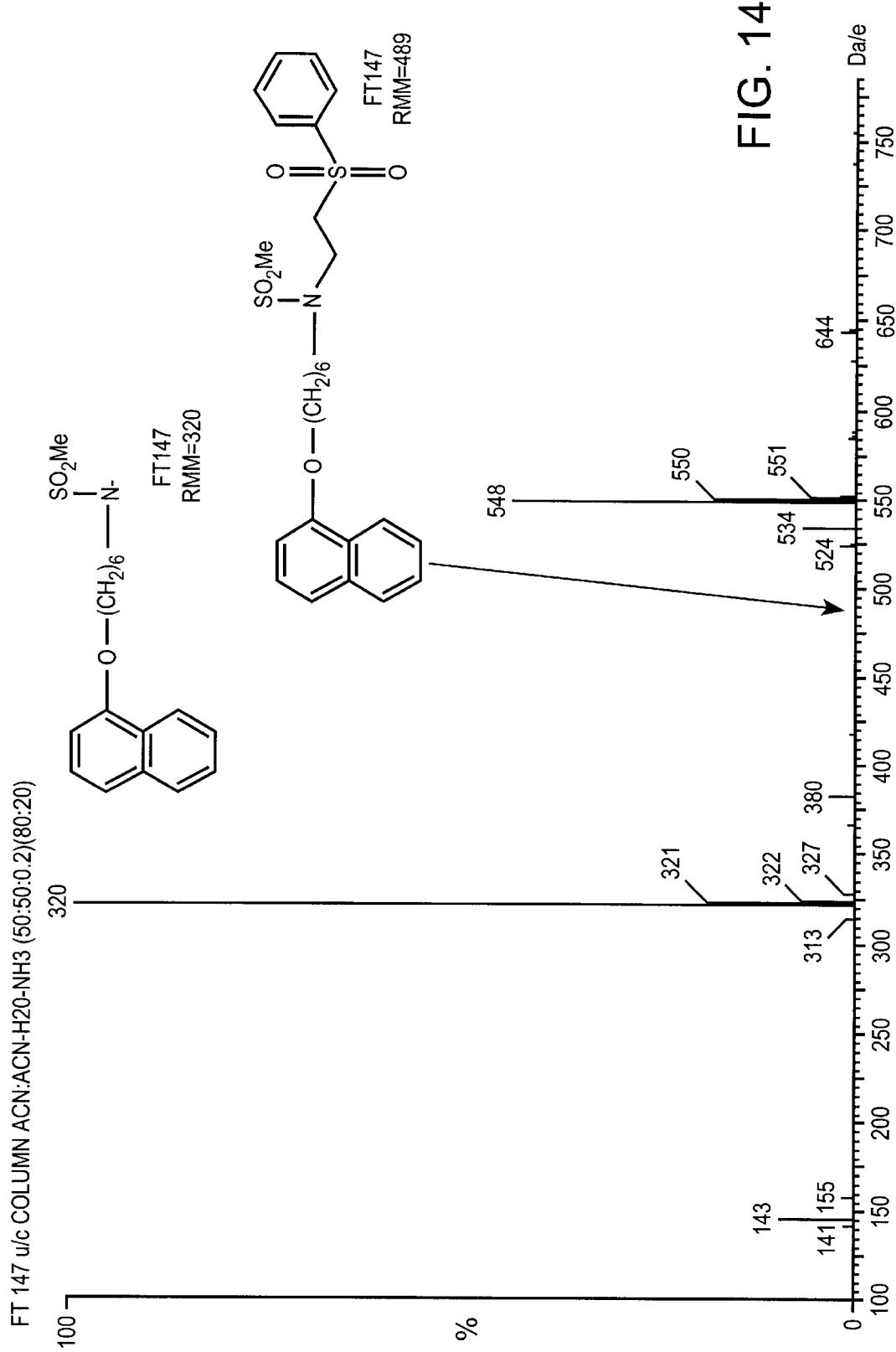
FIG. 14 shows the electrospray mass spectrum of FT147 which is an ether mass marker that is attached to a linker that is cleavable in an electrospray ion source.

Synthesis of eight model mass labels that are cleavable in an electrospray ion source Eight ether compounds were synthesised from commercially available intermediates. These compounds were attached to linkers that cleave in an electrospray ion source. Suitable linkers are disclosed in GB 9815163.2. Two such linkers were used, one which contains a trifluoracetate substitution protecting an amide group and one which contains a mesylate substitution protecting the same amide group in the linker. Each of these linkers was attached to the same set of four ether mass labels to give a total of eight labels. FIG. 6 shows a schematic of the syntheses performed.

The mass labels were synthesised to demonstrate the principle of cleavage of labels in an electrospray ion source. The results show that the nature of the protective group is not essential to the functioning of the cleavable linker and that the nature of the mass label does not interfere with the cleavage process. Thus this linker is compatible with a wide variety of ether and poly-ether mass labels enabling the generation of large arrays of labels.

The markers shown are model markers and are not attached to any analyte molecules. The core of the cleavable linker comprises a phenyl vinyl sulphone. The phenyl ring can be substituted with a bromine group, for example, to permit attachment to 1,7-octadiyne (Aldrich) which can then be used to react the marker group with 5'(4,4'-dimethoxy)trityl-5-iodouridine to generate nucleotide with a mass marker attached to a base. Similarly a brominated phenyl vinyl sulphone can be reacted with propargylic alcohol, which may optionally be O-protected, (Aldrich) which provides a free hydroxyl to attach the mass labels to other positions within a nucleotide using standard methods known in the art. A variety of other groups may be introduced to enable these labels to be reacted with other analytes such as proteins, carbohydrates or other biomolecules.

Synthesis of FT116

A solution of N-benzyloxycarbonyl 6-aminocaproic acid (2.65 g, 10 mmol) in tetrahydrofuran (15 mL) was treated at 0° C. with a 10 M solution of the borane dimethylsulphine complex in tetrahydrofuran (2.2 mL, 22 mmol) and stirred for 1 hour at 0° C. and for 2 hours at room temperature. The reaction mixture was quenched by careful addition of methanol (2 mL). Subsequently the solvents were removed under reduced pressure and coevaporated with methanol (3×20 mL) to give 2.416 g (96%) of FT116. The crude product, which contains a non-polar impurity, was used without further purification in the next step.

An analytically pure sample was prepared by recrystalisation from ethyl acetate/n-hexane.

Confirmation of Identity of FT116 Product

M.p. 79–81° C. Calculated Atomic Composition C 66.90, H 8.42, N 5.57; Measured C 67.17, H 8.68, N 5.67.

$^1$H NMR (CDCl$_3$): 1.35–1.64 (9 H, m), 3.19 (2 H, dt, J=6.5 and 6.5 Hz), 3.62 (2 H, t, J=6.5 Hz), 4.79 (1 H, br s), 5.10 (2 H, s), 7.26–7.37 (5 H, m).

$^{13}$C NMR (CDCl$_3$): 25.31, 26.37, 29.96, 32.57, 40.95, 62.72, 66.64, 128.14, 128.57, 136.76, 156.57.

Mass spectrometry of the compound using Electron Impact Ionisation to ionise the compound gave peaks in the mass spectrum with the following mass to charge ratios: 251 ($M^T$,<1%), 160, 144, 130, 108, 91 (100%).

Synthesis of FT117/2

A solution of FT116 (2.3 g, 9.2 mmol) in dichloromethane (45 mL) and dry triethylamine (5 mL) was treated at 0–5° C. with methanesulphonyl chloride (1.375 g, 12 mmol). The reaction mixture was allowed to warm up to room temperature within 15 minutes and stirred for 4 hours at this temperature, diluted with dichloromethane (50 mL) and washed with a 5% aqueous solution of sodium bicarbonate and water (2×). The organic phase was dried with sodium sulphate and the solvent was removed under reduced pressure. The residue was purified by flash chromatography on silica gel (100 g) using n-hexane/ethyl acetate (1:1) as eluent to furnish 2.413 g (80%) of FT117/2.

Confirmation of Identity of FT117/2 Product

M.p. 24–27° C. Calculated Atomic Composition C 54.69, H 7.04, N 4.25; Measured C 54.88, H 7.07, N 4.21.

$^1$H NMR (CDCl$_3$): 1.32–1.60 (6 H, m), 1.76 (2 H, m), 2.99 (3 H, s), 3.18 (2 H, m), 4.21 (2 H, t, J=6.5 Hz), 4.76 (1 H, br s), 5.10 (2 H, s), 7.26–7.35 (5 H, m).

$^{13}$C NMR (CDCl$_3$): 25.09, 26.08, 29.03, 29.82, 37.42, 40.89, 66.66, 69.84, 128.16, 128.58, 136.75, 156.51.

Mass spectrometry of the compound using Electron Impact Ionisation to ionise the compound gave ions with the following mass to charge ratios: 329 ($M^T$, 3%), 222, 194, 126, 108, 91 (100%).

Synthesis of FT120, FT121, FT122, FT123—General Procedure

A suspension of a 60% oily suspension of sodium hydride (120 mg, 3 mmol) in N,N-dimethylformamide (3 mL) was treated with a solution of the corresponding phenol (3 mmol) in N,N-dimethylformamide (2 mL). After completion of hydrogen evolution a solution of FT117/2 (493 mg, 1.5 mmol) N,N-dimethylformamide (2 mL) was added. The reaction mixture was stirred at room temperature for 18 hours and diluted with diethyl ether/n-hexane (1:1, 25 mL). The solution was washed with water (2×), 1 M aqueous potassium hydroxide (3×10 mL) and water (2×). The organic phase was dried with sodium sulphate and evaporated to dryness. Flash chromatography was carried out on silica gel (20 g) using n-hexane/ethyl acetate (3:1) as eluent to afford the corresponding phenolether.

Confirmation of Identity of FT120 Product

FT120: yield 75%; m.p. 79–81° C. (diethyl ether/n-hexane) Calculated Atomic Composition C 74.44, H 6.97, N 3.34; Measured C 74.51, H 6.98, N 3.32.

$^1$H NMR (CDCl$_3$): 1.34–1.59 (6 H, m), 1.80 (2 H, t, J=6.5 Hz), 3.21 (2 H, dt, J=6.5 and 6.5 Hz), 3.93 (2 H, t, J=6.5 Hz), 4.73 (1 H, br s), 5.10 (2 H, s), 6.81–7.06 (7 H, m), 7.17–7.37 (7 H, m).

$^{13}$C NMR (CDCl$_3$): 25.76, 26.48. 29.22, 29.54, 41.05, 66.66, 68.33, 115.59, 117.68, 120.83, 122.46, 128.15, 128.58, 129.65, 136.77, 150.18, 155.50, 156.49, 158.65.

Mass spectrometry of the compound using Electron Impact Ionisation to ionise the compound gave ions with the following mass to charge ratios: 419 (M$^+$, 5%), 311, 186 (100%), 91, 77.

Confirmation of Identity of FT121 Product

FT121: yield 79%, colourless oil Calculated Atomic Composition H 69.54, H 7.00, N 4.06; Measured C 69.34, H 7.04, N 3.99.

$^1$H NMR (CDCl$_3$): 1.37–1.5 (6 H, m), 1.76 (2 H, t, J=6.5 Hz), 3.20 (2 H, dt, J=6.5 and 6.5 Hz), 3.89 (2 H, t, J=6.5 Hz), 4.73 (1 H, br s), 5.10 (2 H, s), 6.78–6.98 (4 H, m), 7.26–7.37 (5 H, m).

$^{13}$C NMR (CDCl$_3$): 25.72, 26.46, 29.17, 29.94, 41.03, 66.65, 68.49, 115.77, 115.62, 115.93, 128.15, 128.58, 129.65, 136.77, 155.29, 156.49, 158.85.

Mass spectrometry of the compound using Electron Impact Ionisation to ionise the compound gave ions with the following mass to charge ratios: 345 ($M^T$, 5%), 234, 202, 112, 91 (100%).

Confirmation of Identity of FT122 Product

FT122: yield 72%; m.p. 49–51° C. (diethyl ether/n-hexane) Calculated Atomic Composition C 74.33, H 8.22, N 3.94; Measured C 74.61, H 8.33, N 3.88.

$^1$H NMR (CDCl$_3$): 1.25–1.57 (6 H, m), 1.75 (2 H, t, J=6.5 Hz), 2.18 (3 H, s), 2.22 (3 H, s), 3.19 (2 H, dt, J=6.5 and 6.5 Hz), 3.90 (2 H, t, J=6.5 Hz), 4.73 (1 H, br s), 5.10 (2 H, s), 6.61–6.70 (2 H, m), 7.01 (1 H, d, J=8.2 Hz), 7.25–7.36 (5 H, m).

$^{13}$C NMR (CDCl$_3$): 18.72, 19.77, 25.78, 26.49, 29.25, 29.95, 41.06, 66.63, 67.81, 111.52, 116.27, 128.13, 128.58, 130.33, 136.77, 137.92, 156.40, 157.33.

Mass spectrometry of the compound using Electron Impact Ionisation to ionise the compound gave ions with the following mass to charge ratios: 355 (M$^+$, 15%), 264, 246, 212, 122, 121, 107, 91 (100%).

Confirmation of Identity of FT123 Product

FT123: yield 80%; m.p. 42–44° C. (diethyl ether/n-hexane) Calculated Atomic Composition C 76.36, H 7.21, N 3.71; Measured C 76.48, H 7.23, N 3.69.

$^1$H NMR (CDCl$_3$): 1.30–1.63 (6 H, m), 1.93 (2 H, t, J=6.5 Hz), 3.20 (2 H, dt, J=6.5 and 6.5 Hz), 4.11 (2 H, t, J=6.5 Hz), 4.74 (1 H, br s), 5.10 (2 H, s), 6.78 (1 H, d, J=7.3 Hz), 7.24–7.50 (9 H, m), 7.72 (1 H, m), 8.26 (1 H, m).

$^{13}$C NMR (CDCl$_3$): 26.01, 26.55, 29.23, 30.01, 41.09, 66.65, 67.99, 104.67, 120.11, 122.11, 125.15, 125.87, 125.96, 126.39, 127.51, 128.15, 128.58, 134.63, 136.97, 137.92, 154.94, 156.52.

Mass spectrometry of the compound using Electron Impact Ionisation to ionise the compound gave ions with the following mass to charge ratios: 377 ($M^T$, 15%), 269, 234, 165, 144, 127, 115, 91 (100%).

Synthesis of FT126, FT128, FT130, FT132—General Procedure

A solution of the corresponding N-benzyloxycarbonyl-protected phenolether (1 mmol) in methanol (20 mL) was treated with ammonium formate (250 mg, 4 mmol) and 10% Palladium on charcoal (80 mg) and stirred for 15–60 minutes at room temperature. The reaction mixture was filtered through a pad of Celite. The filtrate was concentrated to dryness under reduced pressure. The residue was dissolved in water/ethyl acetate and 1 M potassium hydroxide was added. The organic phase was washed with 1 M potassium hydroxide, water (2x) and dried with sodium sulphate. The solvents were removed under reduced pressure. The corresponding crude amines were used without further purification in the next step.

Synthesis of FT127, FT129, FT131, FT133—General Procedure

A solution of the corresponding amine FT126, FT128, FT130 or FT132 (1 mmol) in methanol (10 mL) was treated with phenyl vinyl sulphone (168 mg, 1 mmol) and triethyl amine (0.05 mL) and refluxed for 2 hours. The solvents were removed under reduced pressure and the residue purified by flash chromatography on silica gel (20 g) with ethyl acetate/triethyl amine (100:1) as eluent to yield the corresponding secondary amine.

Confirmation of Identity of FT127 Product

FT127: yield 82%; colourless oil Calculated Atomic Composition C 68.84, H 6.89, N 3.09; Measured C 69.16, H 7.00, N 3.00.

$^1$H NMR (CDCl$_3$): 1.33–1.49 (6 H, m), 1.75 (2 H, dt, J=16 and 7 Hz), 2.58 (2 H, t, J=7 Hz), 3.02 (2 H, t, J=7 Hz), 3.29 (2 H, t, J=7 Hz), 3.93 (2 H, t, J=7 Hz), 6.85–7.06 (7 H, m), 7.26–7.32 (2 H, m), 7.55–7.69 (3 H, m), 7.91–7.94 (2 H, m).

Mass spectrometry of the compound using Electron Impact Ionisation to ionise the compound gave ions with the following mass to charge ratios: 453 (M$^+$, 3%), 312, 298, 285, 268, 198 (100%), 186, 168, 141, 125, 100, 77.

Confirmation of Identity of FT129 Product

FT129: yield 78%; colourless oil Calculated Atomic Composition C 63.30, H 6.91, N 3.69; Measured C 63.50, H 6.96, N 3.65.

$^1$H NMR (CDCl$_3$): 1.33–1.49 (6 H, m), 1.73 (2 H, dt, J=16 and 7 Hz), 2.57 (2 H, t, J=7 Hz), 3.02 (2 H, t, J=7 Hz), 3.29 (2 H, t, J=7 Hz), 3.90 (2 H, t, J=7 Hz), 6.80–6.85 (2 H, m), 6.92–7.00 (2 H, m), 7.55–7.69 (3 H, m), 7.91–7.94 (2 H, m).

$^{13}$C NMR (CDCl$_3$): 25.92, 26.96, 29.21, 29.87, 43.16, 49.46, 56.16, 68.56, 115.48, 115.61, 115.92, 128.01, 129.40, 133.83, 139.61, 155.33, 158.83.

Mass spectrometry of the compound using Electron Impact Ionisation to ionise the compound gave ions with the following mass to charge ratios: 380 ([M+1]$^+$, 1%), 378 ([M−1], 1%), 287, 268, 198 (100%), 141, 125, 126, 112.

Confirmation of Identity of FT131 Product

FT131: yield 93%; colourless oil Calculated Atomic Composition C 67.83, H 8.02, N 3.60; Measured C 67.89, H 8.06, N 3.55.

$^1$H NMR (CDCl$_3$): 1.31–1.49 (6 H, m), 1.75 (2 H, dt, J=16 and 7 Hz)), 2.18 (3 H, s), 2.22 (3 H, s), 2.56 (2 H, t, J=7 Hz), 3.01 (2 H, t, J=7 Hz), 3.29 (2 H, t, J=7 Hz), 3.91 (2 H, t, J=7 Hz), 6.62 (1 H, dd, J=9 and 2.5 Hz), 6.70 (1 d, J=2.5 Hz), 7.01 (1 H, d, J=9 Hz), 7.55–7.69 (3 H, m), 7.90–7.94 (2 H, m).

$^{13}$C NMR (CDCl$_3$): 18.72, 19.97, 25.97, 26.98, 29.29, 29.89, 43.17, 49.48, 56.17, 67.87, 111.52, 116.27, 128.02, 128.48, 129.41, 130.32, 133.83, 137, 61, 139.61, 157.35.

Mass spectrometry of the compound using Electron Impact Ionisation to ionise the compound gave ions with the following mass to charge ratios: 389 (M$^+$, 2%), 268, 198, (100%), 141, 126, 122, 107.

Confirmation of Identity of FT133 Product

FT133: yield 85%, colourless oil Calculated Atomic Composition C 70.04, H 7.10, N 3.40; Measured C 69.80, H 7.13, N 3.38.

$^1$H NMR (CDCl$_3$): 1.35–1.62 (6 H, m), 1.92 (2 H, dt, J=16 and 7 Hz), 2.56 (2 H, t, J=7 Hz), 3.02 (2 H, t, J=7 Hz), 3.28 (2 H, t, J=7 Hz), 4.13 (2 H, t, J=7 Hz), 6.89 (1 h, dd, J=8 and 1.3 Hz), 7.33–7.68 (7 H, m), 7.78 (1 H, m), 7.90–7.94 (2 H, m), 8.27 (1 H, m).

$^{13}$C NMR (CDCl$_3$): 26.18, 27.00, 29.23, 29.92, 43.18, 49.48, 56.17, 68.02, 104.67, 120.07, 122.11, 125.11, 125.97, 126.37, 127.49, 128.02, 129.39, 133.81, 134, 62, 139.61, 154.96.

Mass spectrometry of the compound using Electron Impact Ionisation to ionise the compound gave ions with the following mass to charge ratios: 411 (M$^+$, 5%), 268, 198 (100%), 144, 126, 125, 115, 100.

Synthesis of FT134, FT135, FT136, FT137—General Procedure

A solution of the corresponding secondary amine FT127, FT129, FT131 or FT133 (0.12 mmol) in dry dichloromethane (2 mL) was treated with triethylamine (0.25 mL) and finally at 0° C. with trifluoroacetic anhydride (0.05 mL, 0.37 mmol). The reaction mixture was stirred at this temperature for 20 min and treated with methanol (0.25 mL). The solvents were evaporated under reduced pressure and the residue was dissolved in dichloromethane and washed with water. The organic extract was dried with sodium sulphate, evaporated to dryness and purified by flash chromatography on silica gel with n-hexane/ethyl acetate (2:1) to furnish the corresponding trifluoroacetamides FT134, FT135, FT136, and FT137.

Confirmation of Identity of FT134 Product

FT134: yield 93%, amorphous solid.

$^1$H NMR (CDCl$_3$): 1.34–1.84 (8 H, m), 3.30–3.48 (4 H, m), 3.76 (2 H, m), 3.95 (2 H, m), 6.84–7.10 (7 H, m), 7.27–7.33 (2 H, m), 7.55–7.73 (3 H, m), 7.90–7.95 (2 H, m).

Mass spectrometry of the compound using Chemical Ionisation with Ammonia in the source to ionise the compound gave ions with the following mass to charge ratios: 567 ([M+NH$_4$]$^-$, 100%), 549 (M$^-$), 475, 427, 399, 381, 186.

Confirmation of Identity of FT135 Product

FT135: yield 82%; amorphous solid.

$^1$H NMR (CDCl$_3$): 1.34–1.82 (8 H, m), 3.30–3.48 (4 H, m), 3.76 (2 H, m), 3.90 (2 H, m), 6.79–6.85 (2 H, m), 6.92–7.00 (2 H, m), 7.55–7.73 (3 H, m), 7.90–7.95 (2 H, m).

MS (CI, NH$_3$): 493 ([M+NH$_4$]$^-$, 100%), 475 (M$^+$), 381, 353, 351, 325, 186.

Confirmation of Identity of FT136 Product

FT136: yield 98%; amorphous solid.

$^1$H NMR (CDCl$_3$): 1.30–1.81 (8 H, m), 2.19 (3 H, s), 2.23 (3 H, s), 3.30–3.48 (4 H, m), 3.77 (2 H, m), 3.92 (2 H, m), 6.64 (1 H, dd, J=9.5 and 2.5 Hz), 6.71 (1 H, d, J=2.5 Hz), 7.02 (1 H, d, J=9.5 Hz) 7.55–7.73 (3 H, m), 7.90–7.95 (2 H, m).

Mass spectrometry of the compound using Chemical Ionisation with Ammonia in the source to ionise the compound gave ions with the following mass to charge ratios: 503 ([M+NH$_4$]$^+$), 485 (M$^-$), 383, 363, 335, 318, 241, 186, 122, 43 (100%).

Confirmation of Identity of FT137 Product

FT137: yield 80%; amorphous solid.

$^1$H NMR (CDCl$_3$): 1.34–1.49 (2 H, m), 1.55–1.72 (4 H, m), 1.87–1.99 (2 H, m), 3.30–3.48 (4 H, m), 3.72 (2 H, m), 4.15 (2 H, m), 6.80 (1 H, dd, J=8.5 and 1.5 Hz), 7.33–7.70 (7 H, m), 7.80 (1 H, m), 7.89–7.94 (2 H, m), 8.27 (1 H, m).

Mass spectrometry of the compound using Chemical Ionisation with Ammonia in the source to ionise the compound gave ions with the following mass to charge ratios: 525 ([M+NH$_4$]$^-$, 100%), 508 ([M+1]$^+$), 385, 383, 357, 340, 186, 160, 140.

Synthesis of FT142, FT143, FT146, FT147—General Procedure

A solution of the corresponding secondary amine FT127, FT129, FT131 or FT133 (0.06 mmol) in dry dichloromethane (2 mL) was treated with triethylamine (0.1 mL) and finally at 0° C. with methanesulphonyl chloride (0.1 mL, 0.13 mmol). The reaction mixture was stirred at this temperature for 20 min and treated with methanol (0.1 mL). The reaction mixture was diluted with dichloromethane and washed with water. The organic extract was dried with sodium sulphate, evaporated to dryness and purified by flash chromatography on silica gel with n-hexane/ethyl acetate (2:3) to furnish the corresponding sulphonamides FT142, FT143, FT146, and FT147.

Confirmation of Identity of FT142 Product

FT142: yield 86%, amorphous solid.

$^1$H NMR (CDCl$_3$) 1.34–1.83 (8 H, m), 2.83 (3 H, s), 3.20 (2 H, t, J=9 Hz), 3.41–3.47 (2 H, m), 3.57–3.62 (2 H, m), 3.94 (2 H, t, J=7 Hz), 6.84–7.07 (7 H, m), 7.62–7.33 (2 H, m), 7.57–7.70 (3 H, m), 7.91–7.95 (2 H, m).

MS (DCI, NH$_3$): 549 ([M+NH$_4$]$^-$, 100%), 531 (M$^-$), 409, 381, 223, 186.

Confirmation of Identity of FT143 Product

FT143: yield 88%, amorphous solid.

$^1$H NMR (CDCl$_3$) 1.30–1.65 (6 H, m), 1.71–1.81 (2 H, m), 2.83 (3 H, 2), 3.19 (2 H, t, J=9 Hz), 3.41–3.47 (2 H, m), 3.56–3.62 (2 H, m), 3.91 (2 H, t, J=7 Hz), 6.79–7.01 (4 H, m), 7.57–7.72 (3 H, m), 7.91–7.95 (2 H, m).

Mass spectrometry of the compound using chemical ionisation to ionise the compound gave ions with the following mass to charge ratios: 475 ([M+NH$_4$]$^-$), 458 ([M+H]$^+$), 363, 307, 238, 186.

Confirmation of Identity of FT146 Product

FT146: yield 89%, amorphous solid.

$^1$H NMR (CDCl$_3$) 1.32–1.63 (6 H, m), 1.70–1.80 (2 H, m), 2.19 (3 H, s), 2.23 (3 H, s), 2.82 (3 H, s), 3.18 (2 H, t, J=9 Hz), 3.41–3.47 (2 H, m), 3.55–3.62 (2 H, m), 3.92 (2 H, t, J=7 Hz), 6.63 (1 H, dd, J=9.5 and 3 Hz), 6.71 (1 H, d, J=3 Hz), 7.02 (1 H, d, J=9.5 Hz), 7.56–7.72 (3 H, m), 7.91–7.95 (2 H, m).

MS (DCI, NH$_3$): 485 ([M+NH$_4$]$^+$, 100%), 467 (M$^+$), 363, 345, 317, 248, 186, 122.

Confirmation of Identity of FT147 Product

FT147: yield 99%, amorphous solid.

$^1$H NMR (CDCl$_3$) 1.35–1.47 (2 H, m), 1.54–1.67 (4 H, m), 1.88–1.98 (2 H, m), 2.81 (3 H, s), 3.20 (2 H, t, J=9 Hz), 3.41–3.47 (2 H, m), 3.55–3.62 (2 H, m), 4.14 (2 H, t, J=7 Hz), 6.80 (1 H, d, J=8.5 Hz), 7.32–7.51 (4 H, m), 7.54–7.7 (3 H, m), 7.80 (1 H, m), 7.91–7.95 (2 H, d, J=8 Hz), 8.27 (1 H, m).

MS (DCI, NH$_3$): 507 ([M+NH$_4$]$^-$), 490 ([M+1]$^+$), 365, 339, 322, 206, 186 (100%).

ESI-MS Analysis of FT 134, 135, 136, 137 and FT 142, 143, 146, 147

The eight compounds FT 134, 135, 136, 137 and FT142, 143, 146, 147 were analysed on a Platform-LC quadrupole instrument (Micromass Ltd, UK) with an electrospray ionisation source. Solutions of each the markers were made up in a 50:50 mixture of water and acetonitrile. Ammonia was also present in the solvent at a concentration 0.2%. FIGS. 7 to 14 show the negative ion mass spectra of FT 134, 135, 136, 137 and FT 142, 143, 146, 147 respectively. In each case there is no detectable molecular ion and a dominant peak in the spectrum corresponding to the negative ion cleavage product is identified. In all of these spectra there are a number of additional peaks. The most significant of these occur at masses corresponding to the molecular mass of the uncleaved marker plus 45 daltons and plus 59 daltons which correspond to adducts of formate and acetate with the uncharged, uncleaved mass label respectively. These were contaminants in the ion source of the mass spectrometer from previous use.

What is claimed is:

1. An array of mass markers, each mass marker in the array comprising an aryl ether, wherein the array comprises a plurality of sets of mass markers, each set of mass markers comprising a plurality of different mass markers, each mass marker in any one set differing in mass from all other mass markers in that set by a mass of at least about 4 Daltons and each mass marker in any one set having the same number of aryl ether units as each of the other mass markers in that set and a different number of aryl ether units from each of the mass markers in any other set.

2. An array according to claim 1, wherein each mass marker in the array comprises an aryl ether monomer, an aryl ether oligomer or an aryl ether polymer.

3. An array according to claim 1, wherein the aryl ether comprises from 1–12 aryl ether units.

4. An array according to claim 1, wherein the aryl ether comprises at least one unsubstituted aryl ether unit.

5. An array according to claim 4, wherein the terminating group of the aryl ether is an unsubstituted aryl ether unit.

6. An array according to claim 1, wherein the aryl ether comprises at least one substituted aryl ether unit.

7. An array according to claim 6, wherein the terminating group of the aryl ether is a substituted aryl ether unit.

8. An array according to claim 6, wherein the substituent group is a fluorine atom, a deuterium atom or a methyl group.

9. An array according to claim 6, wherein the substituent group is a solubilising or a charge carrying group.

10. An array according to claim 9, wherein the solubilising or charge carrying group is —O—Ph—Y where Y is one of —SO$_3^-$, —PO$_4^-$, —PO$_3^-$, CO$_2^-$, —NR$_3^+$, NR$_2$, NH$_2$ or SR$_2^+$ or wherein the solubilising or charge carrying group is the group:

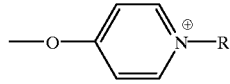

wherein R comprises an alkyl group or an aryl group.

11. An array of mass markers according to claim 1, which array comprises 12 sets of mass markers, each set of mass markers comprising 23 different mass markers, each mass marker in the lightest set of mass markers comprising 1 aryl ether unit and each mass marker in the heaviest set of mass markers comprising 12 aryl ether units.

12. An array of compounds, each compound in the array comprising a different mass marker from an array as defined in claim 1.

13. An array of compounds according to claim 12, each compound in the array having the following formula:

N—L—M wherein N comprises one or more nucleic acid bases, L is either a direct bond between N and M or L comprises a linker moiety, and M comprises the mass marker.

14. An array of compounds according to claim 13, wherein L comprises an oligo-ethylene glycol, a polyethylene glycol, propargylic alcohol, 6-aminohexanol, or a di-ynyl derivative.

15. An array of compounds according to claim 13, wherein L comprises a photo-cleavable, chemically-cleavable or thermally-cleavable linker group.

16. An array of compounds according to claim 15, wherein L comprises a group having the following formula:

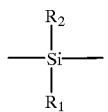

wherein $R_1$ and $R_2$ are substituents selected such that when the compound reacts with an electron donating moiety, either N or M cleaves from the Si atom in preference to $R_1$ and $R_2$.

17. An array of compounds according to claim 16, wherein $R_1$ and $R_2$ are selected such that each has a bond energy to Si greater than the bond energy of N and/or M to Si to ensure that when the compound reacts with an electron donating moiety either N or M cleaves from the Si atom in preference to $R_1$ and $R_2$, and/or $R_1$ and $R_2$, are selected such that their steric bulk is sufficient to ensure that when the compound reacts with an electron donating moiety either N or M cleaves from the Si atom in preference to $R_1$ and $R_2$.

18. An array of compounds according to claim 17, wherein $R_1$ and $R_2$ are independently a hydrogen atom, a halogen atom, a substituent or unsubstituted alkyl group or a substituted or unsubstituted aryl group.

19. An array of compounds according to claim 18, wherein $R_1$ and $R_2$ are each independently fluorine, chlorine, bromine, iodine, methyl, ethyl, propyl, isopropyl, butyl, isobutyl, tert-butyl or phenyl groups.

20. An array of compounds according to claim 16, wherein the electron-donating moiety is a Lewis base.

21. An array of compounds according to claim 20, wherein the Lewis base is ammonia, a primary, secondary or tertiary amine; a compound containing a hydroxy group; an ether; or water.

22. An array of compounds according to claim 15, wherein L comprises a group having the following formula:

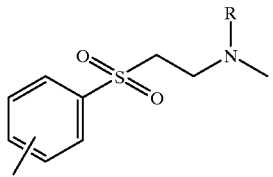

wherein R is an electron withdrawing substituent.

23. An array of compounds according to claim 22, wherein R is a hydrogen atom, a halogen atom, or a substituent comprising a carbonyl group and/or a halogen atom.

24. An array of compounds according to claim 23, wherein R is a fluorine atom, a chlorine atom, a bromine atom, an iodine atom, a trifluoroacetyl group, a trifluoromethyl acetate group, a mesylate group, or a tosylate group.

25. An array of compounds according to claim 13, wherein L is attached to N and/or M by a group as defined in claim 11, or by a —CO—NH— group, an —NH—CO—NH— group, an —NH—CS—NH— group, a —CH$_2$—NH— group, an —SO$_2$—NH— group, an —NH—CH$_2$—CH$_2$— group, or an —OP(=O)(O)O— group.

26. An array of compounds according to claim 13, wherein the group N comprising one or more nucleic acid bases, comprises a nucleotide, an oligonucleotide or a nucleic acid.

27. An array of compounds according to claim 26, wherein the nucleotide, oligonucleotide or nucleic acid is natural, or is modified by modifying a base, sugar and/or backbone of the nucleotide, oligonucleotide or nucleic acid.

28. An array of compounds according to claim 12, wherein the mass marker comprises a metal ion-binding moiety.

29. An array of compounds according to claim 28, wherein the metal ion-binding moiety is a porphyrin, a crown ether, hexahistidine or a multi-dentate ligand.

30. An array of compounds according to claim 12, wherein the mass marker comprises an aryl ether having one or more mass series modifiers, which modifiers affect the mass of the mass marker sufficiently to enable the mass marker to be uniquely resolvable from other mass markers having the same number of aryl ether units by mass spectrometry.

31. An array of compounds according to claim 30, wherein each mass series modifier comprises one or mass series modifying groups which together alter the mass of the mass marker by about 4 Daltons.

32. An array of compounds according to claim 31, comprising a mass marker having from 0–22 mass series modifiers.

33. A method for characterising a nucleic acid or other molecule, which method comprises identifying a mass marker by mass spectrometry, which mass marker is relatable to a specific nucleic acid base or base sequence, or a specific atom or group in a molecule, to identify the mass marker and thereby identify the base or base sequence, or the specific atom or group, wherein the mass marker is a mass marker from an array of mass markers as defined in claim 1.

34. A method according to claim 33, which method further comprises forming a compound which is a compound from an array of compounds, prior to identifying the mass marker, each compound in the array of compounds comprising a different mass marker from an array as defined in claim 1.

35. A method according to claim 34, wherein the method further comprises contacting the compound with an electron donating moiety to cleave the mass marker from the compound.

36. A method according to claim 35, wherein the electron donating moiety is a Lewis base.

37. A method according to claim 34, wherein the method further comprises heating the compound to cleave the mass marker from the compound.

38. A method according to claim 34, wherein the method further comprises introducing the compound into an electrospray ionisation source to cleave the mass marker from the compound.

39. A method according to claim 33, which method further comprises cleaving off the mass marker in the mass spectrometer.

40. A method for characterising a nucleic acid or other molecule, which method comprises identifying a mass marker identifiable by mass spectrometry for the characterisation of a nucleic acid or other molecule, which mass marker is a mass marker from an array of mass markers as defined in claim 1.

41. A method according to claim 40, wherein the nucleic acid or other molecule comprises one or more nucleic acid bases, which comprises a nucleotide, an oligonucleotide or a nucleic acid.

42. A method according to claim 41, wherein the nucleotide, oligonucleotide or nucleic acid is natural, or is modified by modifying a base, sugar and/or backbone of the nucleotide, oligonucleotide or nucleic acid.

43. A method according to claim 40, wherein the mass marker is attached to the nucleic acid or other molecule by a linker group L which comprises a linker moiety.

44. A method according to claim 41, wherein the mass marker is attached to the nucleic acid or other molecule by a linker group L which comprises a linker moiety.

45. A method according to claim 35, wherein the electron donating moiety is the Lewis base is ammonia; a primary, secondary or tertiary amine; a compound containing a hydroxy group; an ether; or water.

* * * * *